(12) United States Patent
Lee et al.

(10) Patent No.: US 9,574,167 B2
(45) Date of Patent: Feb. 21, 2017

(54) METHODS AND APPARATUS FOR INDEPENDENT CONTROL OF PRODUCT AND REACTANT CONCENTRATIONS

(71) Applicant: Pharyx, Inc., Woburn, MA (US)

(72) Inventors: Harry Lee, Malden, MA (US); Kevin Shao-Kwan Lee, Cambridge, MA (US)

(73) Assignee: Pharyx, Inc., Woburn, MA (US)

( * ) Notice: Subject to any disclaimer, the term of this patent is extended or adjusted under 35 U.S.C. 154(b) by 157 days.

(21) Appl. No.: 14/180,403

(22) Filed: Feb. 14, 2014

(65) Prior Publication Data

US 2014/0234954 A1    Aug. 21, 2014

Related U.S. Application Data

(60) Provisional application No. 61/765,224, filed on Feb. 15, 2013.

(51) Int. Cl.
*C12M 1/26* (2006.01)
*C12M 3/06* (2006.01)
*C12M 1/00* (2006.01)

(52) U.S. Cl.
CPC ............ *C12M 33/14* (2013.01); *C12M 23/16* (2013.01); *C12M 47/10* (2013.01)

(58) Field of Classification Search
CPC ....... C12M 23/16; C12M 33/14; C12M 47/10; B01L 2400/0481; B01L 2400/0487; B01L 2400/0638; B01L 2400/0681; B01L 3/50273; B01L 3/502738
See application file for complete search history.

(56) References Cited

U.S. PATENT DOCUMENTS

| 4,278,085 A | 7/1981 | Shim |
| 5,057,432 A | 10/1991 | Wangersky et al. |
| 2004/0124147 A1* | 7/2004 | Fissell, IV ......... A61M 1/3489 210/650 |
| 2012/0065277 A1 | 3/2012 | Balagadde et al. |
| 2013/0084622 A1 | 4/2013 | Ram et al. |
| 2014/0234954 A1* | 8/2014 | Lee ........................ C12M 33/14 435/297.1 |

FOREIGN PATENT DOCUMENTS

WO    WO 2011012725    2/2013

OTHER PUBLICATIONS

Lee et al. U.S. Appl. No. 09/060,107, filed Apr. 15, 2010.
"Plastic-PDMS bonding for high pressure hydrolytically stable active microfluidics.", Lee KS, Ram RJ. Lab Chip. Jun. 7, 2009;9(11):1618-24. doi: 10.1039/b820924c.

* cited by examiner

*Primary Examiner* — William H Beisner
(74) *Attorney, Agent, or Firm* — May Ming Wu

(57) ABSTRACT

A microreactor with a reaction chamber comprising two sub-chambers with reconfigurable volumes, an input conduit with input valve, an un-filtered output conduit with first output valve, and a filtered output conduit with a second output valve is used to perform a method to control a different dilution rate for cells and molecules in continuous culture bioprocesses. In preferred embodiments flow control is achieved using the difference in volume of the two sub-chambers.

20 Claims, 12 Drawing Sheets

METHODS AND APPARATUS FOR INDEPENDENT CONTROL OF PRODUCT AND REACTANT CONCENTRATIONS

RELATED APPLICATIONS

This application claims priority from U.S. Provisional Application 61/765,224, entitled "Methods and apparatus for independent control of product and reactant concentrations", filed Feb. 15, 2013, the content of which is hereby incorporated by reference in its entirety.

TECHNICAL FIELD

The field of the invention relates to apparatus, systems, and methods for continuous cell culture, and continuous bioprocessing.

BACKGROUND OF THE INVENTION

All referenced patents and applications and publications are incorporated herein by reference in their entirety. Furthermore, where a definition or use of a term in a reference, which is incorporated by reference herein is inconsistent or contrary to the definition of that term provided herein, the definition of that term provided herein shall control.

The production of molecules by cells depends on many factors including the growth rate of the cells, the concentration of cells, the concentration of nutrients, the concentration of waste products, and the concentration of desired products. Therefore, a preferred cell culture system for developing cell culture bioprocesses will be able to independently control these factors. In addition, because many experiments may be required to optimize a cell culture bioprocess, a preferred cell culture system will also be able to perform many experiments economically.

A typical bioreactor known in the art can be operated in three modes, batch, fed-batch, and continuous. In batch mode, no additional nutrients are added to the bioreactor throughout the bioreaction. In fed-batch mode, additional nutrients are added and the volume of fluid in the bioreactor can increase throughout the bioreaction. In continuous mode, fluid is added to and removed from the bioreactor so that the volume of fluid in the bioreactor remains nominally constant.

In batch and fed-batch mode, the concentration of cells, the concentration of nutrients, and the concentration of waste and desired products all change over time. This makes batch and fed-batch processes difficult to characterize and specify for product quality control.

Continuous mode cultures come closer to the preferred cell culture system because their operation can generally maintain cell cultures in a steady state condition where the concentration of cells, the concentration of nutrients, and the concentration products remain constant. Continuous mode cultures also have the ability to control metabolic parameters such as the growth rate.

A chemostat is a type of continuous culture where the growth rate is controlled by setting the dilution rate. The dilution rate is the flow rate through the bioreactor divided by the volume of fluid in the bioreactor, both of which are held constant. There is an inflow of fresh nutrient medium and an outflow of the mixed contents of the bioreactor. The chemostat reaches a steady state condition when the cell concentration increases to the point where the number of cells removed in the outflow equals the number of cells that grow from the influx of nutrients from the inflow. Because the number of cells produced per unit time and the number of cells removed per unit time are directly proportional to the cell concentration, in steady state the growth rate equals the dilution rate. The cell growth from the influx of nutrients is determined by the inflow concentration of a limiting nutrient. Therefore, the cell concentration in a chemostat can be controlled by adjusting the concentration of the limiting nutrient.

One limitation of a chemostat is that cells cannot be set to grow near their maximum growth rate because under this condition the cell density decreases and a washout condition can occur where no cells remain in the bioreactor.

To grow cells at their maximum growth rate in continuous culture, turbidostat control is used. In a turbidostat the cell density is controlled by adjusting the dilution rate. When the cell density, as measured by the turbidity of the culture rises above the setpoint, the dilution rate is increased, and when the cell density falls below the setpoint, the dilution rate is decreased. In this mode of culture, the cell density is constant and cells can be maintained at their maximum growth rate.

With the use of a chemostat or a turbidostat a full range of growth rates can be controlled for the cell culture, and the cell density can be controlled, however product concentrations cannot be directly controlled.

In chemostat or turbidostat mode, the product concentrations are determined by the dilution rate, cell density, and cellular product production rate. The product concentrations will change until the product production rate is equal to the product removal rate. The product production rate is equal to the cellular product production rate multiplied by the cell density and the product removal rate is equal to the product concentration multiplied by the outflow rate. Therefore, for a given dilution rate, a higher product production rate will result in a higher product concentration.

The inability to independently control product concentrations is very important when the production rate of a particular product is influenced by the concentration of the product or other products. For example, if production of a protein is inhibited by the concentration of an organic acid and the organic acid production rate is relatively high, for low dilution rates, the organic acid concentration will be relatively high and inhibit the protein production. Another example is if the production of ethanol is highest when the growth rate is low, but the production of ethanol is inhibited by high concentrations of ethanol. In this case, high ethanol productivity cannot be achieved since a low growth rate implies a low dilution rate and a high ethanol concentration.

To better control product concentrations, a bioreactor can be operated in a continuous perfusion mode. In perfusion mode, there is a constant inflow of nutrients and a constant outflow, however cells are prevented from leaving the bioreactor in the outflow. In perfusion mode, the total flow rate through the bioreactor can be set arbitrarily, independent of the growth rate of the cells. As such, the product concentrations can be controlled to the extent that increasing the dilution rate of molecules decreases their concentration. However, in perfusion mode, the concentration of cells will increase until cell growth stops due to nutrient limitation since the nutrient delivery rate is still related to the flow rate. Therefore, while perfusion culture allows more control over product concentration through diluting the molecules and not the cells, a constant cell density cannot be maintained at a non-zero growth rate.

A significant problem with conventional continuous culture systems is their relatively large working volume of 0.5 liters to 10 liters. Because 10 to 100 times the working volume is typically required for an experiment, small working volumes of 100 microliters to 10 mililiters are highly desirable for continuous culture systems, especially if many experiments are conducted for process development.

In order to perform a chemostat, turbidostat, or perfusion culture, a common requirement is the ability to control the flow rate into and out of the bioreactor and to control the volume of fluid within the bioreactor. For conventionally sized bioreactors with volumes on the order of 0.5 liter to 1000 liters, conventional liquid pumps and flow meters can serve to control the fluid flow. To control the volume, many methods are available to measure the liquid volume, such as gravimetric methods or liquid level measurement methods. The liquid volume measurement can then be used to actively remove or add fluid to keep the volume constant. Alternatively, passive methods where fluid above a determined liquid level is not retained in the bioreactor can be used.

However, for small volume bioreactors, with working volumes approximately 100 micro liters to 10 mililiters, fluid flow measurement and control and fluid volume measurement and control are difficult to implement. Such small volume bioreactors are very desirable for continuous culture experiments, however, due to the dramatic reduction in total fluid used in each processing run.

Thus, there remains a considerable need for apparatus and methods that can provide independent control over growth rate, cell density, and product concentrations in continuous culture bioreactors, particularly for small scale bioreactors.

SUMMARY OF INVENTION

The present invention is directed to apparatus and methods to control the dilution of at least two products at different rates during a continuous reaction process in small scale bioreactors.

In preferred embodiments where one product is cells and another product is molecules, a microreactor with a reaction chamber comprising two sub-chambers with reconfigurable volumes, an input port with input valve, an un-filtered output port with first output valve, and a filtered output port with a second output valve performs a method to achieve a different dilution rate for cells and molecules.

A preferred method includes the steps of introducing a first volume of fluid into to the reaction chamber, removing a second volume of fluid through the unfiltered port, introducing a third volume of fluid into the reaction chamber, and removing a fourth volume of fluid through the filtered port. By performing the steps periodically an average flow rate through the unfiltered output port and the filtered output port is achieved. The ratio of the dilution rate of cells to the dilution rate of molecules is adjusted by varying the ratio of the fourth and second volumes, and the average volume is held constant by setting the first volume equal to the second volume and the third volume equal to the forth volume, or more generally, the sum of the first and third volumes equal to the sum of the second and fourth volumes. The ratio of dilution rate of cells to the dilution rate of molecules is also adjusted by varying the frequency of removing output from the filtered port and the frequency of removing output from the filtered port.

In preferred embodiments, a sub-chamber with reconfigurable volume comprises a flexible member whereby deformation of the flexible member changes the volume of the sub-chamber. In preferred embodiments a retaining structure and the flexible member form an upper chamber opposite the sub-chamber and constrains the deformation of the flexible member away from the sub-chamber and defines the maximum volume of the sub-chamber. The minimum volume of the sub-chamber is nominally zero when the flexible member is deformed to conform to the inner surface of the sub-chamber. In a preferred embodiment, deformation of the flexible member is accomplished using air pressure or vacuum in the upper chamber or hydraulic pressure in the sub-chamber to deflect the membrane into the sub-chamber and reduce its volume or deflect the membrane away from the sub-chamber and increase its volume.

In preferred embodiments, the maximum volume of the first sub-chamber is larger than the maximum volume of the second sub-chamber. The difference in volume, delta-V, between the two sub-chambers is used as the volume of fluid introduced and removed from the reaction chamber. In preferred embodiments, an input pump comprises a first pump valve and a second pump valve, where the first and second pump valves are located between the input valve and the reaction chamber and the first pump valve is located between the input valve and the second pump valve. By opening and closing the input valve and pump valves in sequence, a volume of fluid equal to the displacement volume of the first pump valve is injected into the reaction chamber.

In preferred embodiments, the filter enables different dilution rates between the cells and molecules by retaining cells in the reaction chamber while allowing molecules to pass. In preferred embodiments, filters with different properties may be used to achieve different dilution rates for filtered products and products that pass through the filter.

BRIEF DESCRIPTION OF THE DRAWINGS

The embodiments of the present invention will now be described by reference to the following figures, in which identical reference numerals in different figures indicate identical elements and in which.

DETAILED DESCRIPTION OF THE DRAWING

Figure 1A:
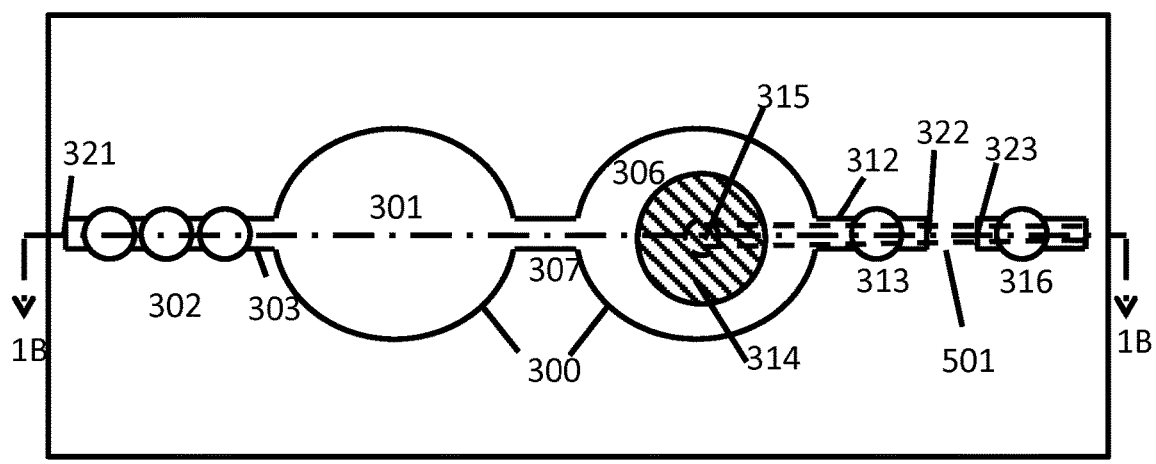
FIG. 1A is a top view of a schematic representation of a microreactor embodiment.

The drawing refers to preferred embodiments of the invention and the particular components, materials, and dimensions, as well as other details are to be interpreted to apply broadly in the art and should not be construed to unduly restrict or limit the invention in any way.

LEGEND FOR DRAWING LABELS

Schematic of a Microreactor Embodiment

- 300 reaction chamber
- 301 first sub-chamber
- 302 input pump
- 303 input conduit
- 304 first upper-chamber
- 305 opening to first upper-chamber
- 306 second sub-chamber
- 307 connecting conduit between first and second sub-chamber
- 308 first flexible member
- 309 second upper-chamber
- 310 opening to second upper-chamber
- 311 second flexible member
- 312 first output conduit
- 313 first output valve
- 314 filter
- 315 second output conduit
- 316 second output valve
- 317 microreactor
- 318 portion of the input conduit under a valve
- 319 flexible membrane of a valve
- 320 valve chamber
- 321 microreactor inlet
- 322 first outlet
- 323 second outlet
- 501 portion of second output conduit below the second sub-chamber
- 401 position of the first flexible member when fluid is introduced into the chamber, increasing the volume above a nominal volume
- 402 position of the second flexible member when fluid is introduced into the chamber, increasing the volume above a nominal volume
- 403 position of the first flexible member that maximizes the volume of the first sub-chamber.
- 404 an intermediate position of the second flexible member when excess fluid prevents the second flexible member from moving to a position that minimizes the volume of the second sub-chamber
- 405 position of the second flexible member that minimizes the volume of the second sub-chamber.

Microreactor Embodiment

- 600 microreactor device
- 610 bottom layer of microreactor embodiment
- 612 inlet to microreactor embodiment
- 614 first outlet
- 616 second outlet
- 617 input valve pressure control inlets
- 618 upper-chamber pressure control inlets
- 619 output valve pressure control inlets
- 620 sub-chamber layer of microreactor embodiment
- 621 first sub-chamber
- 622 second sub-chamber
- 625 filter
- 626 filter pocket
- 627 connecting conduit
- 630 flexible layer of microreactor embodiment
- 631 first flexible member
- 632 second flexible member
- 640 upper-chamber layer of microreactor embodiment
- 641 first upper-chamber
- 642 second upper-chamber
- 644 first pump valve chamber
- 645 second pump valve chamber
- 646 input valve chamber
- 647 first output valve chamber
- 648 second output valve chamber
- 649 pressure control conduit
- 650 top layer of microreactor embodiment.
- 660 input conduit
- 670 first output conduit
- 680 second output conduit Bypass Microreactor Embodiment

- 700 microreactor device
- 710 bottom layer of microreactor embodiment
- 712 inlet to microreactor embodiment
- 714 first outlet
- 716 second outlet
- 717 input valve pressure control inlets
- 718 upper-chamber pressure control inlets
- 719 output valve pressure control inlets
- 720 sub-chamber layer of microreactor embodiment
- 721 first sub-chamber
- 722 second sub-chamber
- 725 filter
- 726 filter pocket
- 727 connecting conduit
- 730 flexible layer of microreactor embodiment
- 731 first flexible member
- 732 second flexible member
- 740 upper-chamber layer of microreactor embodiment
- 741 first upper-chamber
- 742 second upper-chamber
- 744 first pump valve chamber
- 745 second pump valve chamber
- 746 input valve chamber
- 747 first output valve chamber
- 748 second output valve chamber
- 749 pressure control conduit
- 750 top layer of microreactor embodiment.
- 760 input conduit
- 770 first output conduit 780 second output conduit
800 bypass structure
810 first bypass conduit
813 first bypass isolation pressure inlet
815 first bypass isolation valve chamber
820 second bypass conduit
823 second bypass isolation pressure inlet
825 second bypass isolation valve chamber
Flexible Member Position Generator Embodiment
900 flexible member position generator
910 first flexible member position generator unit
911 first 3-way solenoid valve
912 first normally open port
913 first normally closed port
914 first common port=control port
915 first pressure source
916 second 3-way solenoid valve
917 second normally open port
918 second normally closed port
919 second common port
920 second pressure source
950 second flexible member position generator unit In FIG. 1A, a top view of a schematic representation of a microbioreactor embodiment of the present invention is shown. The microreactor 317 sub-chambers 301 and 306 are, for example, polygonal or circular in shape, preferably with rounded corners to reduce stress in the flexible members 308 and 309 when they are deflected into sub-chambers 301, 306, and upper chambers 304, 309. The second output conduit 315 has a portion located below the filter 314 and the dashed lines represent the portion 501 of the second output conduit 315 that is below the second sub-chamber 306.

Figure 1B:
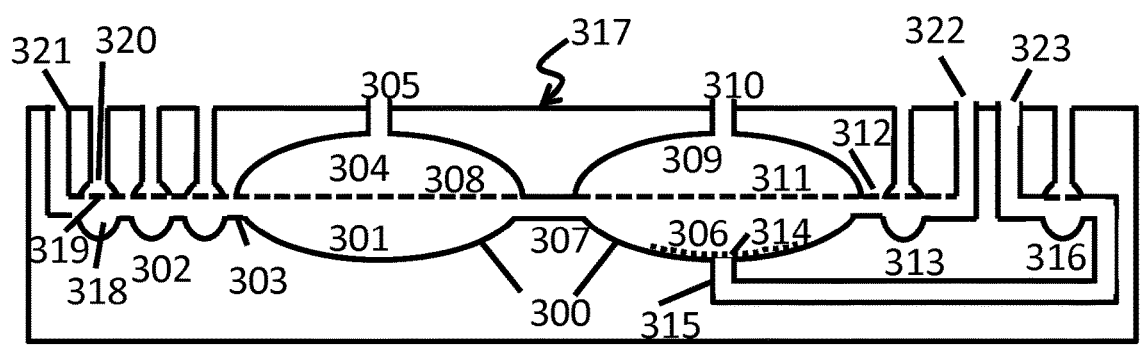
FIG. 1B is a side section view of a schematic representation of a microreactor embodiment.

In FIG. 1B, a side section view of a schematic representation of a microreactor embodiment of the present invention is shown. The microreactor 317 comprises a reaction chamber 300 comprising two sub-chambers 301 and 306. The first sub-chamber 301 is fluidically connected to an input conduit 303 comprising an integrated input pump 302. The input pump comprises three valves, each valve comprising a portion 318 of the input conduit 303; a flexible membrane 319; and a valve chamber 320. Applying a sufficient pressure differential between the valve chamber 320 and the portion 318 of the input conduit 303 deflects the flexible membrane 319 into the portion 318 of the input conduit 303, which prevents fluid flow between the portions of the input conduit on either side of the valve. It should be recognized that for sealing to occur, the cross section of the input conduit must have a shape which allows the deflected flexible membrane to form a seal. An example shape is a portion of a circle closed by a chord of the circle where the length of the chord is larger than the maximum distance between the chord and the portion of the circle. The input pump 302 is connected to the microreactor inlet 321. Above the first sub-chamber 301 is a first upper-chamber 304 which can be pressurized via opening 305. The first sub-chamber 301 and first upper-chamber 304 are separated by a first flexible member 308. A second sub-chamber 306 is fluidically connected to the first sub-chamber 301 via a connecting conduit 307. A second upper-chamber 309 is separated from the second sub-chamber 306 by a second flexible member 311. The second upper-chamber 309 can be pressurized via an opening 310. By alternatively pressurizing the first upper-chamber 304 and the second upper-chamber 309, fluid can be moved between the first sub-chamber 301 and the second sub-chamber 306. The second sub-chamber 306 is fluidically connected to a first output conduit 312 comprising a first output valve 313 to control the flow of fluid through the first outlet 322. At the bottom of the second sub-chamber 306 is a filter 314 which allows fluid with a different composition than a fluid in the reaction chamber 300 to flow through a second output conduit 315. The second output conduit 315 is fluidically connected to a second outlet 323. Since filter 314 is located at the base of the second sub-chamber 306, a portion 501 of the second of the second output conduit is located under the second sub-chamber 306. The second output conduit 315 comprises a second output valve 316 to control the removal of fluid from chamber 300 via the second outlet 323.

Referring in additional detail to FIG. 1B, the microreactor 317 can be comprised of plastic, glass, or metal, with examples such as aluminum, copper, polycarbonate, polystyrene, acrylic, borosilicate glass or any other material known to one of ordinary skill in the art. The first flexible member 308 can be a membrane which can comprise an elastomeric material, for example, having a Young's modulus of less than about 1 GPa. A variety of elastomeric polymeric materials are suitable for making a flexible member 308, 311 including, for example, polymers of the general classes of silicone polymers, epoxy polymers, and acrylate polymers. The input pump 302 valves, first output valve 313, and second output valve 316, can comprise a combination of the microreactor 317 material and the flexible member material, or in some embodiments, just the flexible member material. The filter 314 can comprise a particle filter, for example, with materials such as polycarbonate, acrylic, polyethersulfone, polystyrene, nylon, glass, cellulose, teflon, or any other material known to one of ordinary skill in the art.

In some embodiments, the microreactor 317 can have an area of at least 0.1 inch square, or between 1 inch and 10 inches square, between 10 inches and 100 inches square, or between 3 inches and 9 inches square. The microreactor 317 can also have a thickness 1% to 50% of the square root of the microreactor 317 area, or between 1% and 40%, or between 5% and 30%. The first sub-chamber 301, first upper-chamber 304, second sub-chamber 306, and second upper-chamber 309 can each comprise an area between 5% and 90% of the microreactor 317 area, or between 5% and 75%, or between 10% and 50%. The filter 314 can be a particle filter with pore size between 0.01 micrometers and 10 micrometers, or between 0.05 micrometers and 1 micrometer, or between 0.05 micrometers and 0.5 micrometers. Valve structures 313, 316 in FIG. 1B have a similar structure to the valves of the input pump 302 which comprise a portion 318 of the input conduit 303, a flexible membrane 319, and a valve chamber 320. An input pump valve can be actuated by creating a pressure differential between the portion 318 of the input conduit 318 and the valve chamber 320. The pressure differential can be between 0.1 psi to 30 psi, or between 5 psi and 25 psi, or between 8 psi and 16 psi.

Figure 2A:
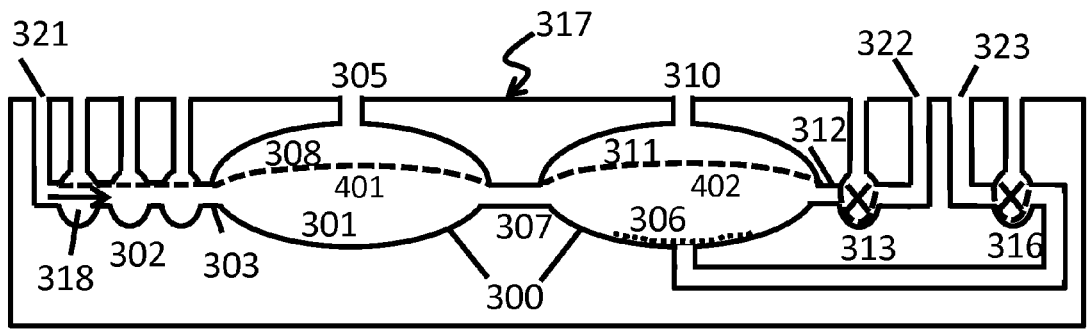
FIG. 2A is an illustration of a first step of a method to operate a schematic representation of a microreactor embodiment.
Figure 2B:
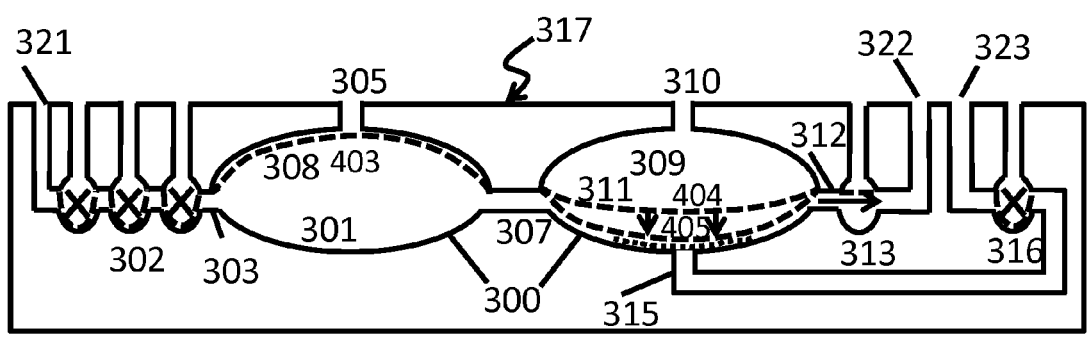
FIG. 2B is an illustration of a second step of a method to operate a schematic representation of a microreactor embodiment.
Figure 2C:
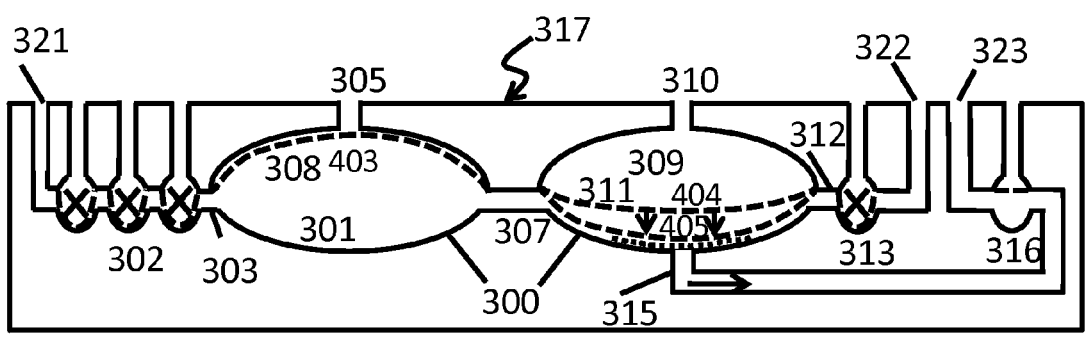
FIG. 2C is an illustration of a third step of a method to operate a schematic representation of a microreactor embodiment.

FIG. 2A, FIG. 2B, FIG. 2C illustrate the steps of an embodiment of a method to operate a microreactor embodiment with independent control over a product concentration and a reactant concentration.

In FIG. 2A, a representation of adding fluid to the reaction chamber 300 is shown. Fluid is introduced into the reaction chamber 300 through the input pump 302. Both the first output valve 313 and the second output valve 316 are closed causing the introduced fluid to move the flexible members 308 and 311 to positions 401 and 402.

In FIG. 2B, a representation of removing fluid from the reaction chamber 300 via the first output conduit 312 is provided. The valves of the input pump 302 are closed and the second upper-chamber 309 is pressurized via the opening 310. Pressurization causes the second flexible member 311 to move to a position 404 and the fluid in the reaction chamber 300 redistributes mostly into the first sub-chamber 301 while the first flexible member 308 moves to position 403 where it is constrained by the upper wall 406 of the first upper-chamber 304. Alternatively, a vacuum pressure can be applied to the first upper chamber 304 to provide an additional driving force to move the first flexible member 308 to position 403. Finally, opening the first output valve 313 allows excess fluid to flow out through the first output conduit 312 while the second flexible member 308 in position 404 moves to position 405. The volume of fluid in the reaction chamber when the first membrane in at the position 403 and the second membrane in the position 405 is determines the nominal volume of the reaction chamber 300.

In FIG. 2C, a representation of removing fluid from the reaction chamber 300 via the second output conduit 315 is provided. The valves of the input pump 302 are closed and the second upper-chamber 309 is pressurized via the opening 310. Pressurization causes the second flexible member 311 to move to a position 404 and the fluid in the reaction chamber 300 redistributes mostly into the first sub-chamber 301 while the first flexible member 308 moves to position 403 where it is constrained by the upper wall 406 of the first upper-chamber 304. Alternatively, a vacuum pressure can be applied to the first upper chamber 304 to provide an additional driving force to move the first flexible member 308 to position 403. Finally, opening the second output valve 316 allows excess fluid to flow out through the filter 314 and the second output conduit 315 while the second flexible member 308 in position 404 moves to position 405.

Figure 3:
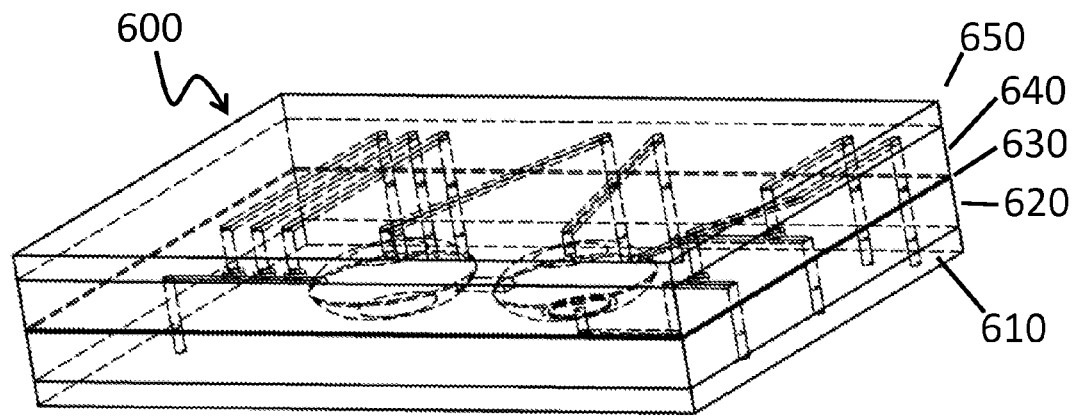
FIG. 3 is an isometric view of a microreactor embodiment.

FIG. 3 shows an isometric view of a microreactor embodiment. The microreactor device 600 comprises a bottom layer 610, a sub-chamber layer 620, a flexible layer 630, an upper-chamber layer 640, and a top layer 650. The microreactor device is preferably 2 inches wide, three inches long, and one half inch thick, but the length, width and height could range from 0.1 to 10 inches. The bottom layer 610, sub-chamber layer 620, upper-chamber layer 640, and top layer 650 are preferably made from polycarbonate although other materials such as acrylic, polypropylene, polyester, aluminum, glass, or other material could be used. The flexible layer 630 is preferably made from a silicone elastomer, and it is contemplated that other elastomer materials such as a polyurethane elastomer, butyl rubber elastomer, or other elastomer material may be used. The flexible layer 630 is preferably 0.004 inches thick, and it is contemplated that other thicknesses such as between 0.0001 and 0.004 inches, or between 0.004 and 0.01 inches, or between 0.0001 and 0.1 inches, or between 0.01 inches and 0.1 inches thick, could be used. The top layer 650 is preferably approximately 0.04 inches thick, and other thicknesses such as between 0.01 inches and 0.04 inches, or between 0.04 inches and 0.1 inches, or between 0.01 and 0.5 inches, or between 0.1 inches and 1 inch could be used. The device layers are bonded together to form the microreactor device 600. The device layers other than the flexible layer 630 are preferably bonded using a silicone pressure sensitive adhesive. Other adhesives are contemplated such as acrylic adhesives, rubber adhesives, or other adhesive are contemplated as are other bonding methods such as thermal diffusion bonding, solvent bonding, ultrasonic welding, or other bonding method are contemplated. The flexible layer 630 is bonded to the other layers using a chemical primer on the polycarbonate layers and corona treating the flexible layer 630 to form strong, hydrolytically stable bonds as described in "Plastic-PDMS bonding for high pressure hydrolytically stable active microfluidics.", Lee K S, Ram R J. Lab Chip. 2009 Jun. 7; 9(11):1618-24. doi: 10.1039/b820924c. Other bonding methods using different surface treatments are also contemplated. The flexible layer 630 is preferably fabricated by spin coating an uncured liquid elastomer which then cures to form a solid elastomer film. Other fabrication methods are contemplated such as knife coating, gravure coating, or other coating methods can be used to fabricate the flexible layer 630.

Figure 4:
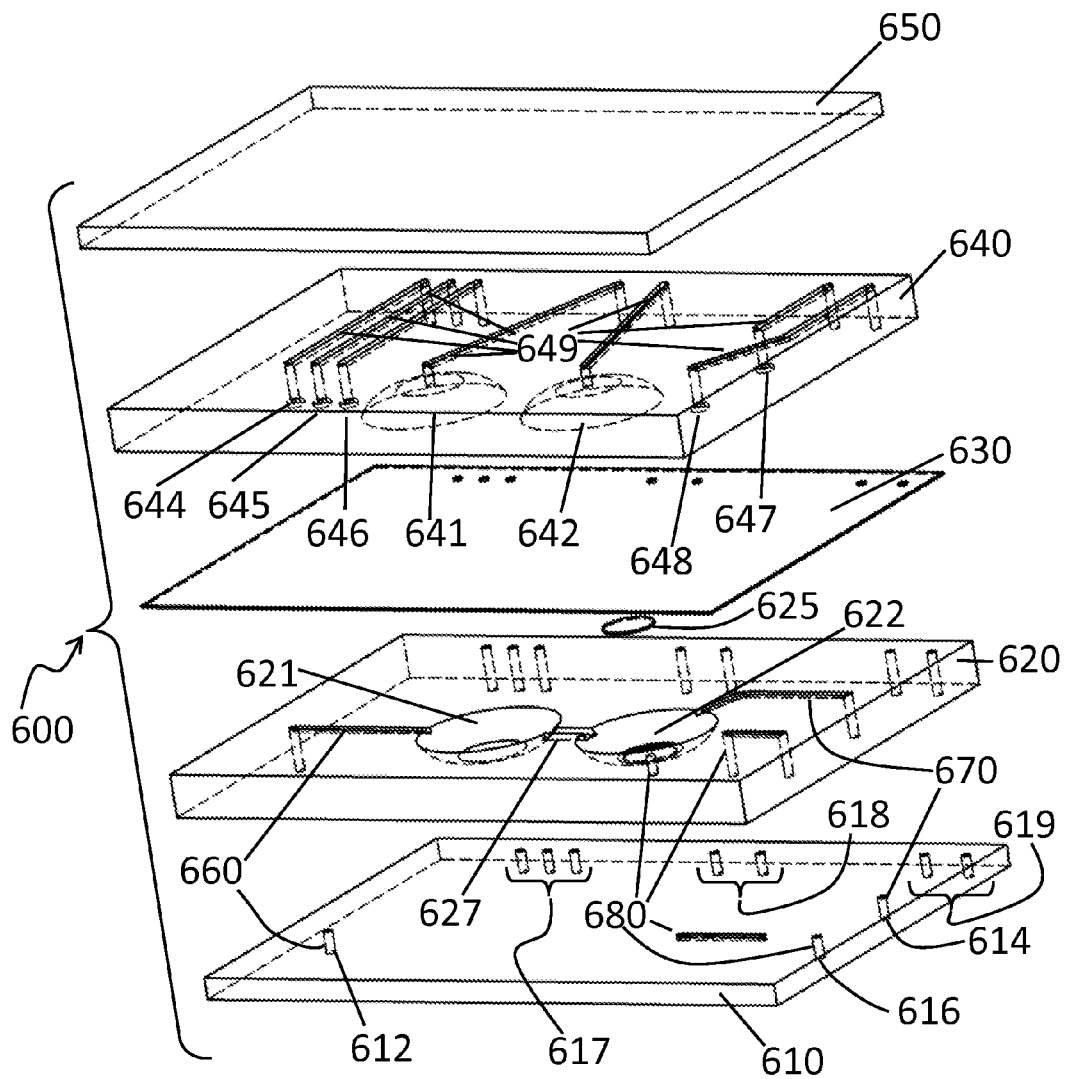
FIG. 4 is an exploded view of the microreactor embodiment shown in FIG. 3.

FIG. 4 shows an exploded view of the microreactor embodiment shown in FIG. 3. to more clearly show the microreactor device 600 structures. An input conduit 660 comprises portions of the input conduit in the bottom layer 610 and the sub-chamber layer 620. The input conduit 660 fluidically connects an inlet 612 to a first sub-chamber 621. A first output conduit 670 comprises portions of the output conduit in the bottom layer 610 and sub-chamber layer 620. The first output conduit 670 fluidically connects the second sub-chamber 622 with a first outlet 614. A second output conduit 680 comprises portions of the second output conduit in the bottom layer 610 and the sub-chamber layer 620. The second output conduit 680 fluidically connects the second side of a filter 625 to a second outlet 616. A connecting conduit fluidically connects the first sub-chamber 621 to the second sub-chamber 622. The upper-chamber layer 640 comprises a first upper-chamber 641, a second upper chamber, 642, a first pump valve chamber 644, a second pump valve chamber 645, an input valve chamber 646, a first output valve chamber 647, and a second output valve chamber 648. When the layers of the microreactor device are bonded together, the valve chambers 644-648 are positioned over conduits 660, 670, 680 and define valves over their respective conduits. The portions of the flexible layer 630 coinciding with the position of the valve chambers are flexible members that can deflect into the respective conduits, when the valve chambers are pressurized, and prevent fluid flow between the portions of the respective conduits on either side of the deflected flexible member. The upper-chamber layer 640 further comprises pressure control conduits 649 connecting the input valve chambers 644-646 to input valve pressure control inlets 617, the upper-chambers 641-642 to upper-chamber pressure control inlets 618 and the output valve chambers 647-648 to output valve pressure control inlets 619. In this embodiment, the microreactor reaction chamber comprises the first sub-chamber 621, the second sub-chamber 622, and the connecting conduit 627.

Figure 5A:
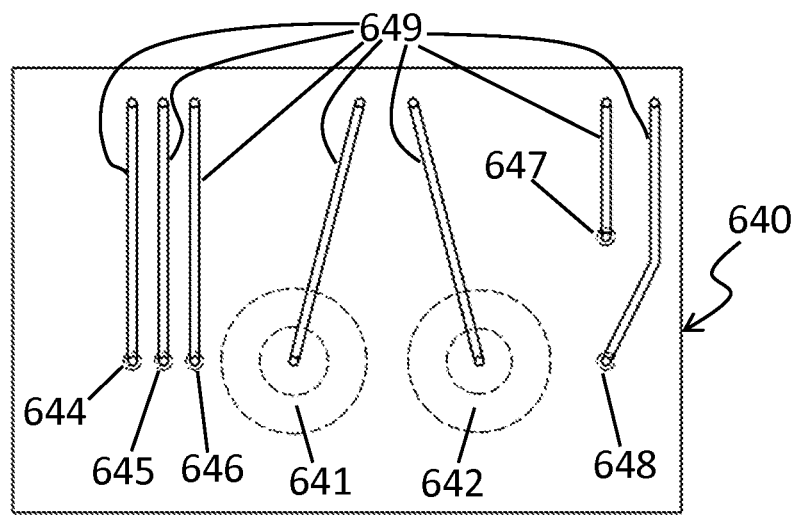
FIG. 5A is a top view of an upper-chamber layer of the microreactor embodiment shown in FIG. 3.

FIG. 5A shows a top view of an upper-chamber layer 640 of the microreactor embodiment shown in FIG. 3. Portions of the pressure control conduits 649 on the top surface of the upper chamber layer 640 are indicated along with the valve chambers 644-648 and upper-chambers 641 and 642 that are shown with dashed lines indicating they are on the bottom surface of the upper-chamber layer. The pressure control conduits 649 and valve control chambers 644-648 and upper chambers 641-642 are preferably fabricated by CNC machining but other methods of fabrication such as molding or embossing or other fabrication methods are contemplated. The pressure control conduits 649 are preferably 0.031 inches wide and 0.030 inches deep, but other dimensions such as between 0.01 inches and 0.1 inches or between 0.1 inches and 0.5 inches or between 0.01 and 0.5 inches for the width and depth are contemplated. The valve control chambers 644-648 are preferably circular with a diameter of 0.0625 inches and a depth of 0.005 inches, but other dimensions are contemplated including a depth between 0.001 inches and 0.1 inches or between 0.1 inches and 1 inch or between 0.001 inches and 1 inch, a diameter between 0.010 inches and 0.1 inches or between 0.1 inches and 1 inch or between 0.01 inches and 1 inch. Alternative shapes of the valve control chambers are also contemplated including polygonal shapes, or any closed shape. The upper-chambers 641-642 are preferably circular 0.75 inches in diameter and 0.1 inches deep, but other shapes and dimensions are contemplated such as any closed contour, preferably without internal convexity, with an area between 0.125 square inches and 6 square inches and depths between 0.01 inches and 1 inch. The upper-chamber layer 640 is preferably approximately 0.1 inches thick, and other thicknesses such as between 0.01 inches and 0.5 inches or between 0.05 inches and 0.1 inches, or between 0.1 inches and 1 inch or between 0.01 inches and 1 inch could be used.

Figure 5B:
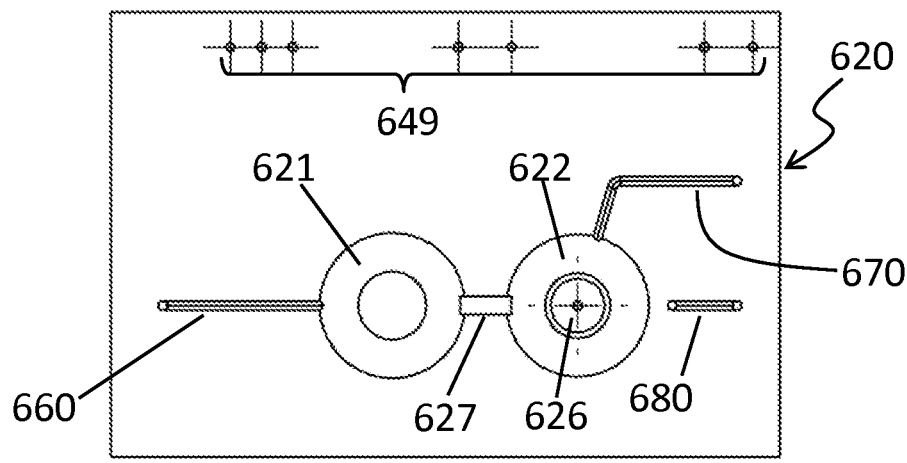
FIG. 5B is a top view of a sub-chamber layer of the microreactor embodiment shown in FIG. 3.

FIG. 5B shows a top view of a sub-chamber layer 620 of the microreactor embodiment 600 shown in FIG. 3. The sub-chamber layer 620 comprises the first sub-chamber 621, the second sub-chamber 622, the connecting conduit 627, a portion of the input conduit 660, a portion of the first output conduit 670, a portion of the second output conduit 680, and a portion of the pressure control conduits 649. The sub-chamber layer 620 further comprises a filter pocket 626 at the bottom of the second sub-chamber 622. The filter 625 is bonded to the filter pocket such that fluid passing through the second output conduit 680 must pass through the filter 625. The dimensions of the sub-chambers 621 and 622 are preferably the same as the dimensions of the upper chambers 641 and 642 in FIG. 5A, however alternative shapes and dimensions are also contemplated such as any closed contour, preferably without internal convexity, with an area between 0.125 square inches and 6 square inches and depths between 0.01 inches and 1 inch. In addition, sub-chamber dimensions different than the upper chamber dimensions are contemplated. In addition sub-chamber dimensions which are different from each other are also contemplated. A preferred embodiment would have the volume of the composite cavity defined by the first sub-chamber and first upper-chamber be different than the volume of the composite cavity defined by the second sub-chamber and second upper-chamber. This volume difference is preferably 10 microliters, although other volume differences such as volumes in the range of 100 nano liters to 1 microliter, 1 microliter to 10 microliters, 10 microliters to 100 microliters, 100 microliters to 1 mL and 1 mL to 10 mL. The connecting conduit 627 is preferably 0.05 inches wide and 0.02 inches deep and 0.25 inches long however other dimensions are contemplated including widths and depths ranging between 0.001 inches and 1 inch and lengths between 0.01 inches and 10 inches. The portions of the input conduit 660, first output conduit 670, and second output conduit 680 on the top surface of the sub-chamber layer 620 preferably have a semi-circular cross section preferably the cross section obtained by machining a channel into a flat substrate using, for example, a ball end mill with a 0.0625 inch diameter and a depth of 0.005 inches. This semi-circular cross section is an embodiment of a cross section that will allow the flexible member of a membrane pinch valve to seal against the conduit and prevent fluid flow between the portions of the conduit on either side of the valve. It is also contemplated that portions of the conduit that do not comprise a valve may have a different cross sectional shape such as a rectangular shape. The lengths of the portions of the input conduit 660, first output conduit 670, and second output conduit 680 are preferably between 0.1 inches and 1 inches long, but may have any length between 0.01 inches and 20 inches. The filter pocket is preferably circular with 0.25 inches in diameter and 0.01 inches deep, but other shapes and depths are contemplated including any shape enclosed by a closed contour and a depth between 0.001 inches and 1 inch. The sub-chamber layer 620 is preferably approximately 0.1 inches thick, and other thicknesses such as between 0.01 inches and 0.5 inches or between 0.05 inches and 0.1 inches, or between 0.1 inches and 1 inch or between 0.01 inches and 1 inch could be used.

Figure 5C:
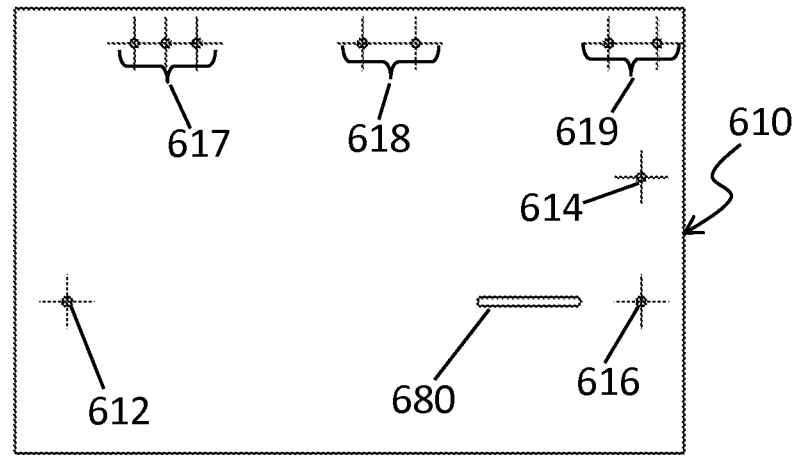
FIG. 5C is a top view of a bottom layer of the microreactor embodiment shown in FIG. 3.

FIG. 5C shows a top view of a bottom layer 610 of the microreactor embodiment 600 shown in FIG. 3. The bottom layer 610 comprises a portion of the second output conduit 680, a portion of the input conduit 660 (see FIG. 4) a portion of the first output conduit 670 (see FIG. 4) and an inlet 612, a first outlet 614, a second outlet 616, input valve pressure control inlets 617, upper-chamber pressure control inlets 618, and output valve pressure control inlets 619. Preferably the bottom layer is interfaced to a manifold to provide the pressure control signals into the pressure control inlets 617-619, and fluid conduits for the input conduit and output conduits. The lengths of the portions of the input conduit 660, first output conduit 670, and second output conduit 680 are preferably between 0.1 inches and 1 inches long, but may have any length between 0.01 inches and 20 inches. The bottom layer 610 is preferably approximately 0.1 inches thick, and other thicknesses such as between 0.01 inches and 0.5 inches or between 0.05 inches and 0.1 inches, or between 0.1 inches and 1 inch or between 0.01 inches and 1 inch could be used.

Figure 6A:
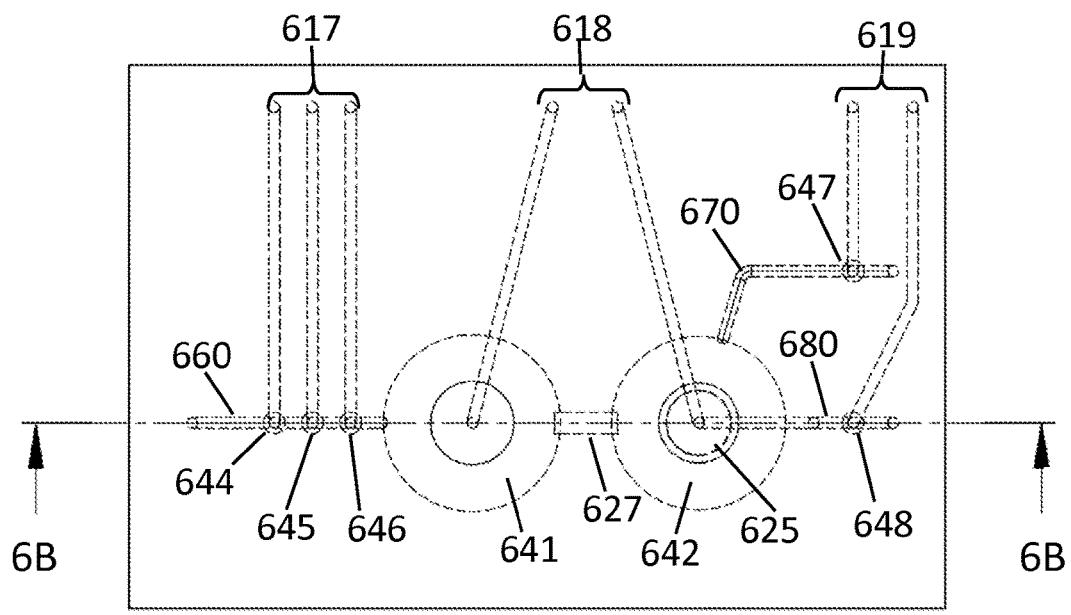
FIG. 6A is a top view of the microreactor embodiment shown in FIG. 3.

FIG. 6A shows a top view of the microreactor embodiment shown in FIG. 3 where hidden lines are shown as dashed lines. The section line 6B-6B passes through the input conduit 660, the valve chambers 644, 645, 646, 648, the upper chambers 641 and 642, the connecting conduit 627, and the second output conduit 680.

Figure 6B:
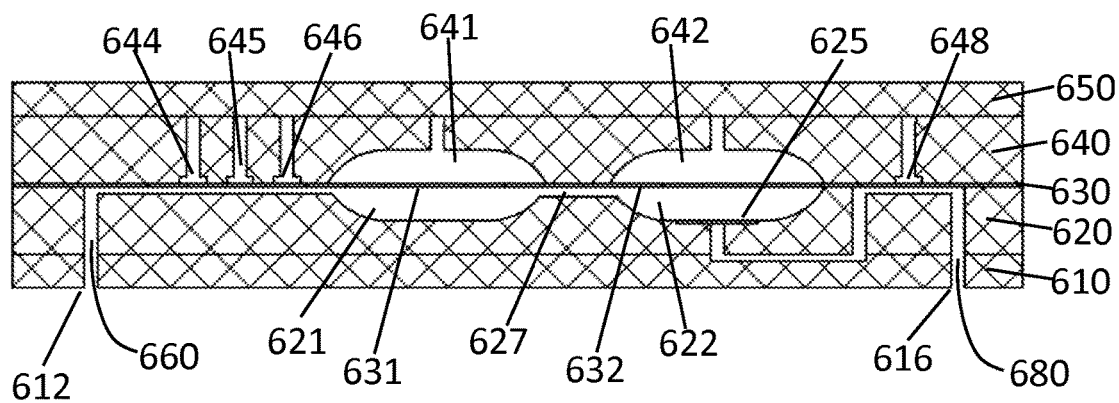
FIG. 6B is a section view of FIG. 6A along the section line 6B-6B.

FIG. 6B shows a section view of FIG. 6A along the section line 6B-6B in FIG. 6A. A first flexible member 631 is a portion of the flexible layer 630 defined by the perimeter of the first upper-chamber 641. In a preferred embodiment, the first flexible member 631 is a shared boundary of the first sub-chamber 621 and first upper-chamber 641. Configuring the pressure in the first upper chamber 641 to be higher than the hydrostatic pressure in the first sub-chamber 621 can drive the first flexible member 631 towards the bottom of the first sub-chamber 621. Conversely, configuring the pressure in the first upper chamber 641 to be lower than the hydrostatic pressure in the first sub-chamber 621 can drive the first flexible member 631 towards the top of the first upper-chamber 641. A second flexible member 632 is a portion of the flexible layer 630 defined by the perimeter of the second upper-chamber 642. In a preferred embodiment, the second flexible member 632 is a shared boundary of the second sub-chamber 622 and second upper-chamber 642. Configuring the pressure in the second upper chamber 642 to be higher than the hydrostatic pressure in the second sub-chamber 622 can drive the second flexible member 632 towards the bottom of the second sub-chamber 622. Conversely, configuring the pressure in the second upper chamber 642 to be lower than the hydrostatic pressure in the second sub-chamber 622 can drive the second flexible member 632 towards the top of the second upper-chamber 642.

Figure 7:
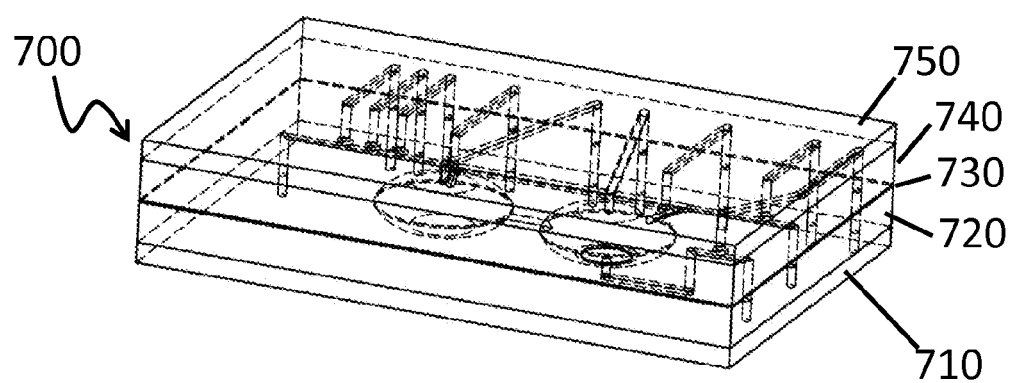
FIG. 7 is an isometric view of a bypass microreactor embodiment.

FIG. 7 shows an isometric view of a bypass microreactor embodiment 700 comprising a bottom layer 710, a sub-chamber layer 720, a flexible layer 730, an upper-chamber layer 740, and a top layer 750. Many of the structures and labels in FIG. 7 thru FIG. 10C are analogous to the structures and labels in FIG. 3 thru FIG. 6B. For clarity, when the description of FIG. 7 thru FIG. 10C refers to component with an analogous component in the description of FIG. 3 thru FIG. 6B, the last two digits of the label will be the same and the words used to reference the components will be the same.

Figure 8:
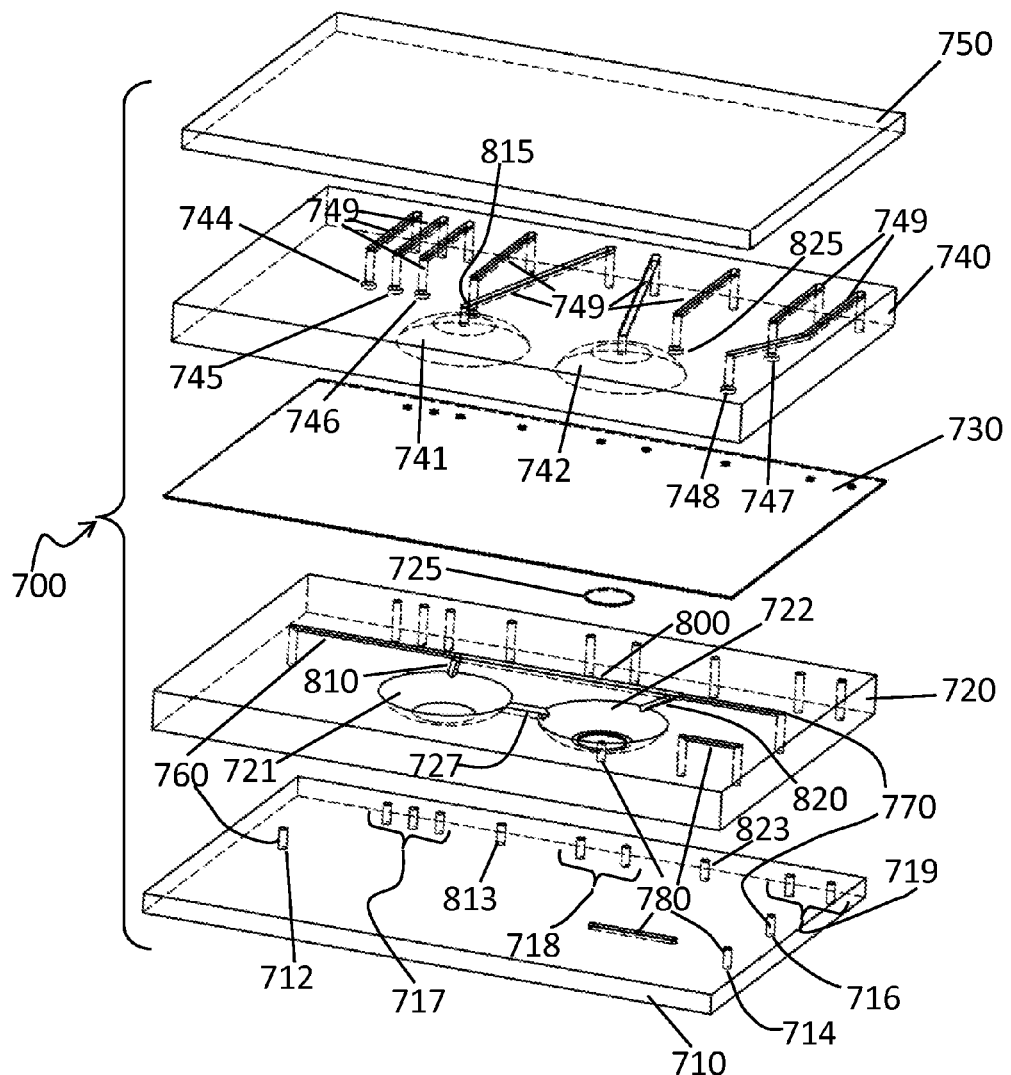
FIG. 8 is an exploded view of the bypass microreactor embodiment shown in FIG. 7.

Referring now to FIG. 8 which shows an exploded view of the bypass microreactor embodiment 700, the distinguishing features of the bypass microreactor embodiment can be clarified. The sub-chamber layer 720 comprises: a first sub-chamber 721; a second sub-chamber 722; a connecting conduit 727 fluidically connecting the first 721 and second 722 sub-chambers; a bypass structure 800; a first bypass conduit 810 fluidically connecting a first portion of the bypass structure to the first sub-chamber 721; and a second bypass conduit 820 fluidically connecting a second portion of the bypass structure to the second sub-chamber 722; a portion of an input conduit 760 fluidically connecting an inlet 712 to the first portion of the bypass structure 800; a portion of a first output conduit 770 fluidically connecting the second portion of the bypass structure 800 to a first outlet 716; a filter 725; and a portion of a second output conduit 780 fluidically connecting the second side of the filter 725 to a second outlet 718. In this bypass microreactor embodiment, the reaction chamber comprises: the first sub-chamber 721; the second sub-chamber 722; the connecting conduit 727; the bypass structure 800; the first bypass conduit 810; and the second bypass conduit 820.

The upper-chamber layer 740 comprises: a first upper-chamber 741; a second upper chamber 742; a first pump valve chamber 744; a second pump valve chamber 745; an input valve chamber 746; a first output valve chamber 747; a second output valve chamber 748; a first bypass isolation valve chamber 815; and a second bypass isolation valve chamber 825. When the layers of the microreactor device are bonded together, the valve chambers 744-748 and 815, 825 are positioned over conduits 760, 770, 780, 810, 820 and define valves over their respective conduits. The portions of the flexible layer 730 coinciding with the position of the valve chambers are flexible members that can deflect into the respective conduits, when the valve chambers are pressurized. The deflected flexible members prevent fluid flow between the portions of the respective conduits on either side of the deflected flexible member. The upper-chamber layer 740 further comprises pressure control conduits 749 connecting the input valve chambers 744-646 to input valve pressure control inlets 717, the upper-chambers 741-742 to upper-chamber pressure control inlets 718; the output valve chambers 747-748 to output valve pressure control inlets 719; and the bypass isolation valve chambers 815, 825 to a first 813 and second 823 bypass isolation pressure control inlet.

Figure 9A:
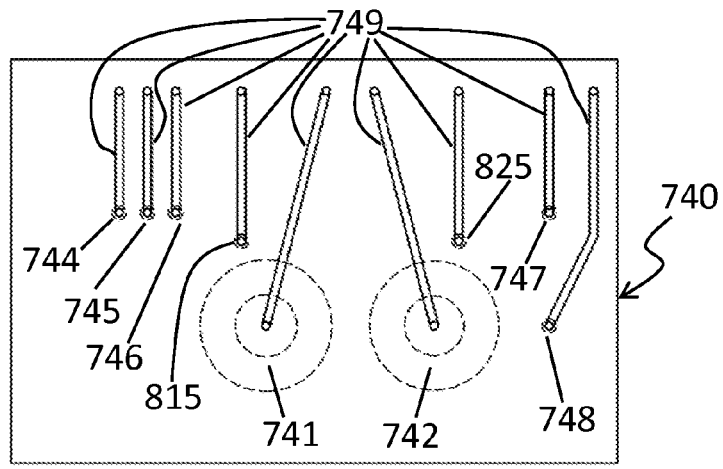
FIG. 9A is a top view of an upper-chamber layer of the bypass microreactor embodiment shown in FIG. 7.

FIG. 9A shows a top view of an upper-chamber layer 740 of the bypass microreactor embodiment 700 shown in FIG. 7. Portions of the pressure control conduits 749 on the top surface of the upper chamber layer 740 are indicated along with the valve chambers 744-748, 815, 825 and upper-chambers 741 and 742 that are shown with dashed lines indicating they are on the bottom surface of the upper-chamber layer. The pressure control conduits 749 and valve control chambers 744-748, 815, 825 and upper chambers 741-742 are preferably fabricated by CNC machining but other methods of fabrication such as molding or embossing or other fabrication methods are contemplated. The pressure control channels are preferably 0.031 inches wide and 0.030 inches deep, but other dimensions such as between 0.01 inches and 0.1 inches or between 0.1 inches and 0.5 inches or between 0.01 inches and 0.5 inches for the width and depth are contemplated. The valve control chambers 644-648 are preferably circular with a diameter of 0.0625 inches and a depth of 0.005 inches, but other dimensions are contemplated including a depth between 0.001 inches and 0.1 inches or between 0.1 inches and 1 inch or between 0.001 inches and 1 inch, a diameter between 0.010 inches and 0.1 inches or between 0.1 inches and 1 inch or between 0.01 inches and 1 inch. Alternative shapes of the valve control chambers are also contemplated including polygonal shapes, or any closed shape. The upper-chambers 641-642 are preferably circular 0.75 inches in diameter and 0.1 inches deep, but other shapes and dimensions are contemplated such as any closed contour, preferably without internal convexity, with an area between 0.125 square inches and 6 square inches and depths between 0.01 inches and 1 inch. The upper-chamber layer 640 is preferably approximately 0.1 inches thick, and other thicknesses such as between 0.01 inches and 0.5 inches or between 0.05 inches and 0.1 inches, or between 0.1 inches and 1 inch or between 0.01 inches and 1 inch could be used.

Figure 9B:
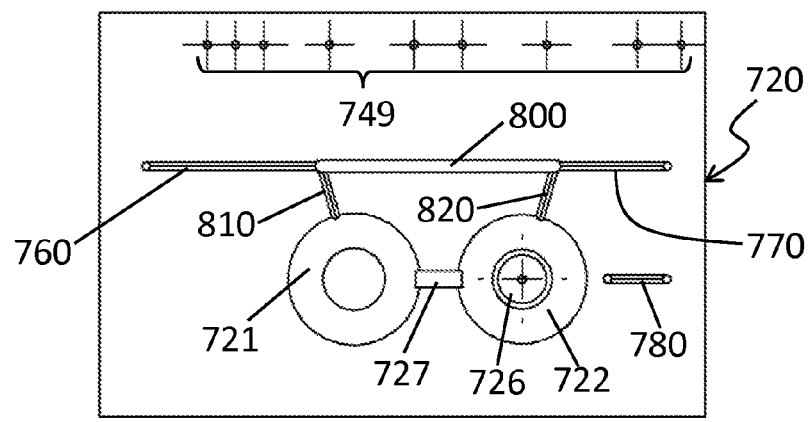
FIG. 9B is a top view of a sub-chamber layer of the bypass microreactor embodiment shown in FIG. 7.

FIG. 9B shows a top view of a sub-chamber 720 layer of the bypass microreactor embodiment 700 shown in FIG. 7. The sub-chamber layer 720 comprises: the first sub-chamber 721; the second sub-chamber 722; the connecting conduit 727; a portion of the input conduit 760; a portion of the first output conduit 770; a portion of the second output conduit 780; a portion of the pressure control conduits 749; a bypass structure 800; a first bypass conduit 810; and a second bypass conduit 820. The sub-chamber layer 720 further comprises a filter pocket 726 at the bottom of the second sub-chamber 722. The filter 725 is bonded to the filter pocket such that fluid passing through the second output conduit 780 must pass through the filter 725. The dimensions of the sub-chambers 721 and 722 are preferably the same as the dimensions of the upper chambers 741 and 742 in FIG. 5A, however alternative shapes and dimensions are also contemplated such as any closed contour, preferably without internal convexity, with an area between 0.125 square inches and 6 square inches and depths between 0.01 inches and 1 inch. The connecting conduit 727 is preferably 0.05 inches wide and 0.005 inches deep and 0.25 inches long however other dimensions are contemplated including widths and depths ranging between 0.001 inches and 1 inch and lengths between 0.01 inches and 10 inches. The portions of the input conduit 760, first output conduit 770, second output conduit 780, the first bypass conduit 810, and the second bypass conduit 820, on the top surface of the sub-chamber layer 720 preferably have a semi-circular cross section preferably the cross section obtained by machining a channel into a flat substrate using, for example, a ball end mill with a 0.0625 inch diameter and a depth of 0.005 inches. This semi-circular cross section is an embodiment of a cross section that will allow the flexible member of a membrane pinch valve to seal against the conduit and prevent fluid flow between the portions of the conduit on either side of the valve. It is also contemplated that portions of the conduit that do not comprise a valve may have a different cross sectional shape such as a rectangular shape. The lengths of the portions of the input conduit 760, first output conduit 770, second output conduit 780, and the lengths of the first bypass conduit 810, and the second bypass conduit 820, are preferably between 0.1 inches and 1 inches long, but may have any length between 0.01 inches and 20 inches. The flow resistance of the connecting conduit should be comparable or higher than the flow resistance of each bypass conduit to facilitate circulation of fluid through the bypass structure when the bypass isolation valves are open. Alternatively an additional valve to allow increasing the flow resistance of the connecting channel, on demand could be used. It should be clear to one of ordinary skill in the art that a reduction of the flow resistance of the bypass conduits could be achieved by increasing the spatial dimensions of the bypass conduits or using multiple bypass conduits in parallel. The bypass structure 800 is preferably an elongated chamber with one spatial dimension at least ten times larger than either of the other two spatial dimensions of the chamber. The large spatial dimension of the bypass structure is preferably 1 inch but may range from 0.1 to 10 inches. The filter pocket is preferably circular with 0.25 inches in diameter and 0.01 inches deep, but other shapes and depths are contemplated including any shape enclosed by a closed contour and a depth between 0.001 inches and 1 inch. The sub-chamber layer 720 is preferably approximately 0.1 inches thick, and other thicknesses such as between 0.01 inches and 0.5 inches or between 0.05 inches and 0.1 inches, or between 0.1 inches and 1 inch or between 0.01 inches and 1 inch could be used.

Figure 9C:
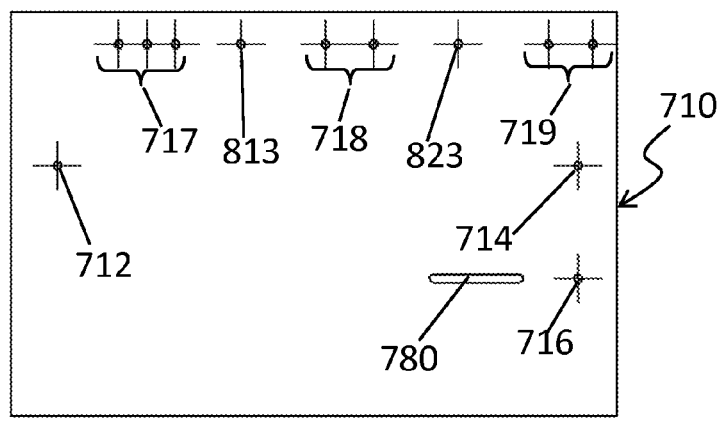
FIG. 9C is a top view of a bottom layer of the bypass microreactor embodiment shown in FIG. 7.

FIG. 9C shows a top view of a bottom layer of the bypass microreactor embodiment 700 shown in FIG. 7. The bottom layer 710 comprises a portion of the second output conduit 780, a portion of the input conduit 760 (see FIG. 8) a portion of the first output conduit 770 (see FIG. 8) and an inlet 712, a first outlet 714, a second outlet 716, input valve pressure control inlets 717, upper-chamber pressure control inlets 718, output valve pressure control inlets 719, a first bypass isolation pressure control inlet 813, and a second bypass isolation pressure control inlet 823. Preferably the bottom layer is interfaced to a manifold to provide the pressure control signals into the pressure control inlets 717-719, 813, 823 and fluid conduits for the input conduit and output conduits. The lengths of the portions of the input conduit 760, first output conduit 770, and second output conduit 780 are preferably between 0.1 inches and 1 inches long, but may have any length between 0.01 inches and 20 inches. The bottom layer 710 is preferably approximately 0.1 inches thick, and other thicknesses such as between 0.01 inches and 0.5 inches or between 0.05 inches and 0.1 inches, or between 0.1 inches and 1 inch or between 0.01 inches and 1 inch could be used.

Figure 10A:
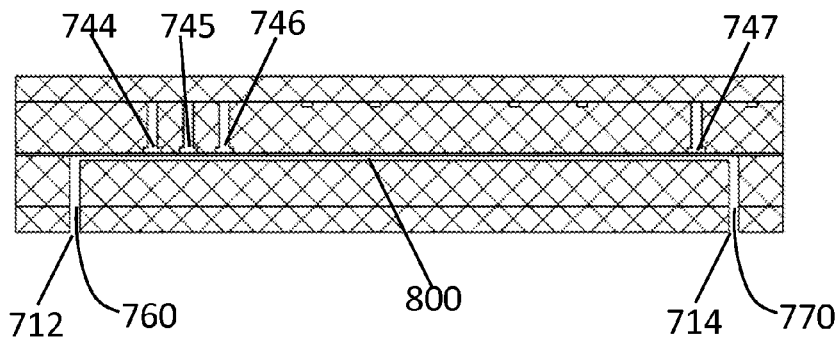
FIG. 10A is a section view of FIG. 10B along the section line 10A-10A.
Figure 10B:
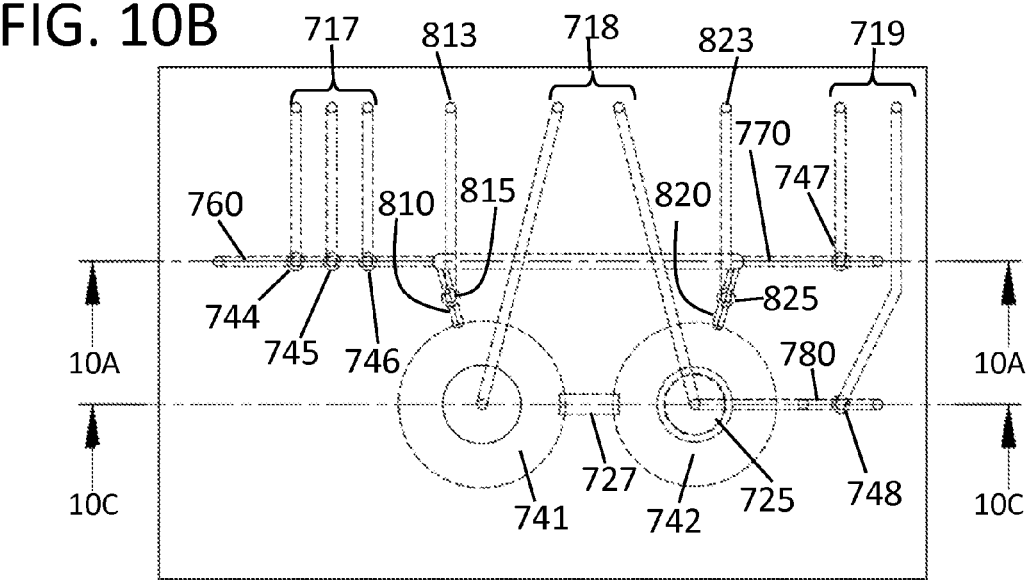
FIG. 10B is a top view of the bypass microreactor embodiment shown in FIG. 7.

FIG. 10A shows a section view of FIG. 10B along the section line 10A-10A which intersects the input conduit 760, the bypass structure 800, and the first output conduit 770. The three valve structures defined by the first pump valve chamber 744, the second pump valve chamber 745, and the input valve chamber 746 compose an input pump. When a pressurized fluid source is applied at inlet 712, opening and closing the input pump valves in a sequence, 744 open/745 open/746 closed; 744 closed/745 open/746 closed; 744 closed/745 open/746 open; 744 closed/745 closed/746 open; 744 closed/745 closed 746 closed. Moves a volume of fluid approximately equal to the displaced volume of the valve defined by valve chamber 745 through the input conduit.

FIG. 10B shows a top view of the bypass microreactor embodiment 700 shown in FIG. 7.

Figure 10C:
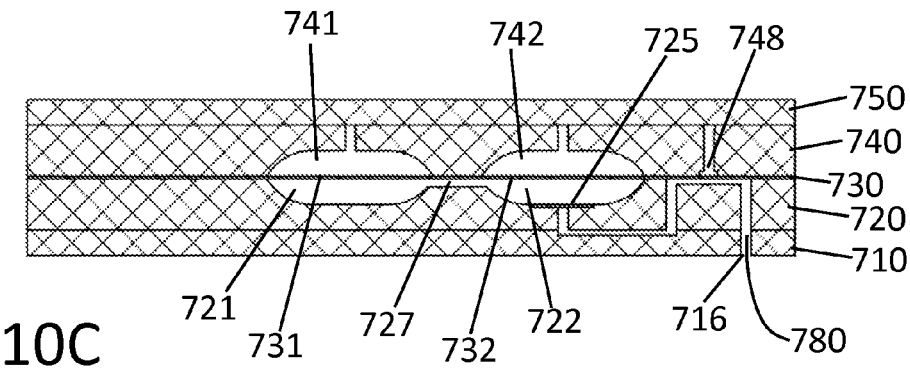
FIG. 10C is a section view of FIG. 10B along the section line 10C-10C.

FIG. 10C shows a section view of FIG. 10B along the section line 10C-10C which intersects the first 721 and second 722 sub-chambers. A first flexible member 731 is a portion of the flexible layer 730 defined by the perimeter of the first upper-chamber 741. In a preferred embodiment, the first flexible member 731 is a shared boundary of the first sub-chamber 721 and first upper-chamber 741. Configuring the pressure in the first upper chamber 741 to be sufficiently higher than the hydrostatic pressure in the first sub-chamber 721 can drive the first flexible member 731 towards the bottom of the first sub-chamber 721. Conversely, configuring the pressure in the first upper chamber 741 to be sufficiently lower than the hydrostatic pressure in the first sub-chamber 721 can drive the first flexible member 731 towards the top of the first upper-chamber 741. It should be noted that a sufficient pressure differential is required to overcome the elastic strain in the flexible member. A second flexible member 732 is a portion of the flexible layer 730 defined by the perimeter of the second upper-chamber 742. In a preferred embodiment, the second flexible member 732 is a shared boundary of the second sub-chamber 722 and second upper-chamber 742. Configuring the pressure in the second upper chamber 742 to be sufficiently higher than the hydrostatic pressure in the second sub-chamber 722 can drive the second flexible member 732 towards the bottom of the second sub-chamber 722. Conversely, configuring the pressure in the second upper chamber 742 to be sufficiently lower than the hydrostatic pressure in the second sub-chamber 722 can drive the second flexible member 732 towards the top of the second upper-chamber 742. It should be noted that a sufficient pressure differential is required to overcome the elastic strain in the flexible member.

The bypass structure 800 and valves defined by the bypass isolation valve chambers 815 and 825 enable the microreactor to be operated in a mode where the introduction of a first fluid through the input conduit 760 and the removal of a second fluid through the first output conduit 770 can be accomplished simultaneously. During ordinary operation, the valves defined by the bypass isolation valve chambers 815 and 825 are open while the input and output valves are closed. The flexible members 731 and 732 are alternately deflected into their respective sub-chambers to move the fluid between the two sub-chambers 721 and 722. If the flow resistance of the bypass conduits 810 and 820 are comparable to the flow resistance of the connecting conduit 727, fluid will flow through the bypass structure and the composition of the fluid throughout the bypass structure and the sub-chambers will be homogeneous. To introduce a volume of fluid through the input conduit and simultaneously remove fluid from the first output conduit, the bypass isolation valves are closed, the first output valve is opened, and the input pump is operated. The shape of the bypass structure is chosen so the fluid flow remains in the laminar flow regime which ensures that a volume equal to the introduced volume will flow out the first output conduit as the input pump operates. The volume introduced by the input pump is set to be less than the total volume of the bypass structure to prevent the introduced fluid from directly flowing out the first output conduit. To complete the cycle, the input and output valves are closed and the bypass isolation valves are opened.

Figure 11A:
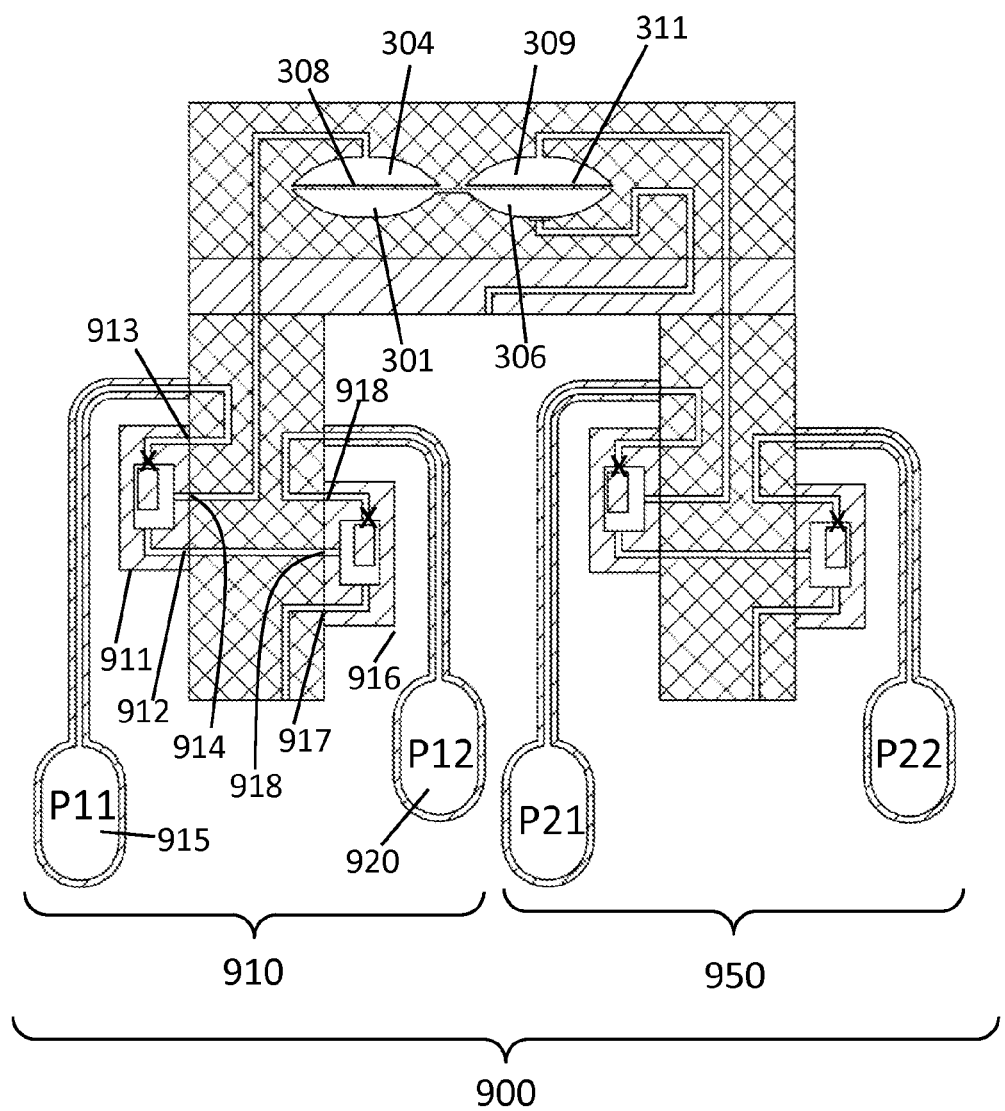
FIG. 11A is a schematic section view of a microreactor embodiment with a flexible member position generator in a second configuration.
Figure 11B:
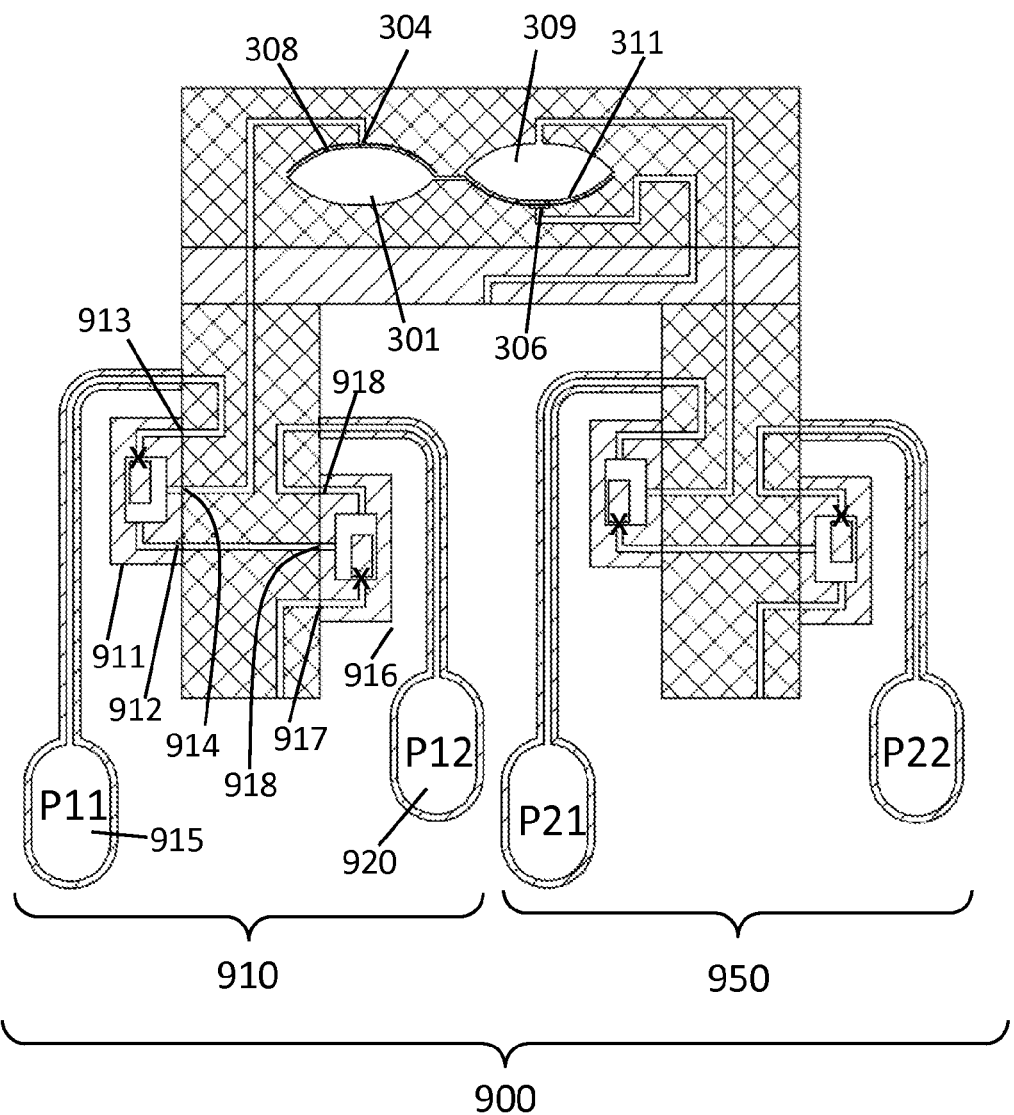
FIG. 11B is a section view of a microreactor embodiment with a flexible member position generator in a first configuration.

FIG. 11A and FIG. 11B show a schematic section view of a system comprising a microreactor embodiment and an embodiment of a flexible member position generator 900. Wherein said microreactor embodiment comprises: a first sub-chamber 301; a first upper-chamber 304; a second sub-chamber 306; a second upper-chamber 309; a connecting conduit 307; and a second output conduit 315. The flexible member position generator 900 comprises a flexible member position generator unit 910, 950 comprising: a first 3-way solenoid valve 911 comprising a first normally open port 912, a first normally closed port 913, a first common port 914, a first passive state where the first normally open port 912 and first common port 914 are fluidically connected, and a first energized state where the first normally closed 913 port and first common 914 port are fluidically connected; and a first pressure source 915 fluidically connected to the first normally closed port 913. A flexible member position generator unit 910, 950 can optionally further comprise: a second 3-way solenoid valve 916 comprising a second normally open port 917, a second normally closed port 918, a second common port 919, a second passive state where the second normally open port and second common port are fluidically connected, and a second energized state where the second normally closed port and second common port are fluidically connected; and a second pressure source 920 fluidically connected to the second normally closed port. Wherein the first normally open port 912 is fluidically connected to the second common port 918, the second normally open port 917 is vented to atmosphere, and the first common port 914 is the control port of the flexible member position generator unit 910, 950. If the second 3-way solenoid valve option is not used, the first normally open port is vented to atmosphere.

Considering FIG. 11A and FIG. 11B in more detail, the flexible member position generator embodiment comprises: a first flexible member position generator unit 910 with first pressure source 915 at a pressure P11, second pressure source 920 at a pressure P12, and control port 914 fluidically connected to the first upper-chamber 304; and a second flexible member position generator unit 950 with first pressure source at a pressure P21, second pressure source at a pressure P22, and control port fluidically connected to the second upper chamber. The pressures P11 and P21 are preferably in a range 0 psig-15 psig and the pressures P12 and P22 are preferably in a range −15 psig and 0 psig. One skilled in the art would know that the pressures P11, P21, P12, and P22 need only be configured such that the desired flexible member positions can be achieved.

In FIG. 11A the flexible member position generator embodiment is in a second configuration where the state of the first and second 3-way solenoid switch of the first flexible member position generator unit are passive and the state of the first and second 3-way solenoid switch of the second flexible member position generator unit are passive. In this condition the first and second upper chambers are vented to atmosphere.

FIG. 11B the flexible member position generator embodiment is in a first configuration where the state of the first 3-way solenoid switch of the first flexible member position generator is passive, the state of the second 3-way solenoid switch of the second flexible member position generator is energized, the state of the first 3-way solenoid switch of the second flexible member position generator is energized, and the state of the second 3-way solenoid switch of the second flexible member position generator is passive. In this condition the first flexible member 308 is in a position which maximizes the volume of the first sub-chamber 301 and the second flexible member 311 is in a position which minimizes the volume of the second sub-chamber 306.

EXAMPLES

A first embodiment is a polycarbonate microreactor with a 1 milliliter reaction chamber. The microreactor input conduit comprises an integrated three valve peristaltic pump. The reaction chamber comprises two sub-chambers, sub-chamber A and sub-chamber B, connected by a connecting conduit. Each sub-chamber has a 500 microliter nominal volume and an upper chamber with a 500 microliter nominal volume, separated by a flexible silicone membrane. When the upper-chamber is pressurized, the flexible silicone membrane deflects into the sub-chamber, reducing the volume of the sub-chamber and displacing fluid out of the sub-chamber and into the adjacent sub-chamber via the connecting conduit. Since the sub-chamber and upper-chamber are similar volume, when silicone membrane A is deflected, removing most of the fluid in the sub-chamber A, most of the gas in upper-chamber B is removed to accommodate the fluid volume from sub-chamber A. Therefore, at the nominal reactor volume, when membrane A is fully deflected into sub-chamber A, most to all of the fluid is in sub-chamber B where sub-chamber B is approximately 1 milliliter in volume and upper-chamber B is approximately 0 milliliters in volume. This is true for the reverse case as well. The input conduit with the three valve input pump is connected to sub-chamber A. Two output conduits, C and D, each comprising an output valve, are connected to sub-chamber B. Output C is directly connected to sub-chamber B while Output D is connected through a cellulose or polyethersulfone particle filter with pore size 200 nanometers located at the base of sub-chamber B. To operate the microreactor to control cell density, first the cell concentration in the reactor is measured. This can be accomplished by passing light through either sub-chamber A or sub-chamber B and measuring the change in intensity of light passing through the cells in the reactor and light not passing through the cells in the reactor. Next, silicone membranes A and B are relaxed and fluid is introduced from the input pump to reduce the cell concentration to a lower desired cell concentration. Membranes A and B are deflected alternately to mix the fluid in chambers A and B together by changing the pressure in upper-chambers A and B. Then only membrane B is deflected. Since the volume is now larger than the nominal volume of the culture chamber, membrane B will not be able to remove all of the fluid from sub-chamber B. Then output valve C is opened, allowing the remaining fluid from sub-chamber B to be removed, returning the total culture chamber volume to the nominal volume. Since output C is not filtered, removing the extra volume does not change the cell concentration of the culture chamber. Output valve C is then closed. Next both membrane A and B are relaxed and fluid is introduced from the input pump again. Then optionally, membranes A and B are deflected alternately to mix the fluid in chambers A and B together by changing the pressure in upper-chambers A and B. Next only membrane B is deflected. This time, the excess volume is removed by opening output valve D. Since output D is blocked by a particle filter, cells are not allowed to pass and only cell-free media is removed through output D. After the reactor volume has returned to the nominal volume, the cell concentration has also nominally returned to the cell concentration before the second input from the peristaltic pump. Then output valve D is closed. This cycle is repeated periodically with a period of 1 minute to maintain a nominally constant cell concentration in the reactor.

In the case where it is known that the filter resistance is high enough to reduce flow through the filter to less than the desired flow rate when configured to remove fluid through output D, output conduit D and the filter are reconfigured such that the filter is located at the base of sub-chamber A and output D is connected to sub-chamber A instead of sub-chamber B. All steps of the first embodiment are performed as previously described. In another aspect, the present invention relates to a method to perform a biochemical reaction in a reaction chamber with a flow of fluid into and out of the reaction chamber, where a product concentration can be controlled independently of the flow of fluid into and out of the reaction chamber. The method comprises the steps: Z) introducing a first volume of a first fluid into the reaction chamber that reduces the product concentration in the reaction chamber fluid; Y) removing a second volume of a second fluid from the reaction chamber, resulting in nominally either no change or a decrease in the product concentration in the reaction chamber fluid; X) introducing a third volume of a third fluid into the reaction chamber reducing the product concentration in the reaction chamber fluid; and W) removing a fourth volume of a fourth fluid from the reaction chamber through a filter resulting in an increase in the product concentration in the fluid in the reaction chamber.

To summarize, the first volume of the first fluid nominally introduces fresh reactants into the reaction chamber, which dilutes the existing product in the reaction chamber; the second volume removes, from the reaction chamber and not through a filter, the second fluid with a composition the same as the reaction chamber fluid which leaves the product concentration unchanged; the third volume of the third fluid nominally introduces fresh reactants with fluid composition the same or different from the composition of the first fluid, which dilutes the product in the reaction chamber; and the fourth volume removes, from the reaction chamber and through a filter, a fourth fluid with a composition different than the reaction chamber fluid composition. Nominally the composition of the fourth fluid has zero product concentration, which increases the concentration of product in the reaction chamber.

In this example, the product can be cells.

When performing the method, the sum of the volumes of the introduced fluids nominally equals the sum of the volumes of the removed fluids. The composition of the introduced fluids can be varied by combining source fluids in varying proportions. A fluid can be a single fluid or a combination of two or more fluids since a combination of multiple fluids results in another fluid.

The order in which the steps of the method are performed is arbitrary and steps may even be performed simultaneously.

In a preferred embodiment, a general chemostat cycle comprises performing step Y and step Z.

In a preferred embodiment, a general perfusion cycle comprises performing step X and step W.

In a preferred embodiment, the general chemostat cycle may be performed repeatedly with a first time interval between performing each general chemostat cycle and the general perfusion cycle may be performed repeatedly with a second time interval between performing each general perfusion cycle. This mode of operation is a chemostat-perfusion combination. The ratio of the dilution rate of cells and the dilution rate of molecules is given by the flow rate out of the non-filtered output divided by the total flow rate out of both outputs.

The method may also comprise an additional step V) measure the concentration of cell in the reaction chamber.

In a preferred embodiment, a general turbidostat cycle comprises performing step V to determine if the cell concentration is higher than a target cell concentration. If the cell concentration is higher than the target, step Y and step Z are performed.

In a preferred embodiment, the general turbidostat cycle may be performed repeatedly with a first time interval between each general turbidostat cycle and the general perfusion cycle may be performed repeatedly with a second time interval between each general perfusion cycle. This mode of operation combines a turbidostat with perfusion. In this mode, the ratio of the dilution rate of cells and the dilution rate of molecules is given by the flow rate out of the non-filtered output divided by the total flow rate out of both outputs.

In the general case, the first, second, third, and fourth volumes, and the composition of the first and third fluids may be chosen as a function of measured parameters of the reaction, and the time interval between performing groups of steps of the method may be constant or varying.

The reaction chamber volume can be between 100 microliters and 1000 liters, or between 1 microliters and 10 milliliters, or between 50 microliters and 5 milliliters. The product in the reaction chamber can be a chemical, biochemical, bacteria cell, yeast cell, salt, protein, or any other substance known to one skilled in the art. The first and third introduced fluid volumes can each be between 0% and 10% of the reaction chamber fluid volume, or between 0% and 50% of the reaction chamber fluid volume. The first and third fluid volumes can be introduced into the reaction chamber from a fluid source using known methods to one skilled in the art, for example, a peristaltic pump, a syringe pump, or using a pressure difference between the fluid source and the reaction chamber and controlling the fluid flow with one or more valves. The pressure difference can be generated using gravity, air pressure, a mechanical pump, or any other method of generating a pressure difference known in the art. In addition, other methods to introduce fluid into the reaction chamber may be used. The second volume and fourth volume can be removed by using known methods to one skilled in the art, for example, a peristaltic pump, a syringe pump, or using a pressure difference between the reaction chamber and a fluid sink, and controlling the fluid flow with one or more valves. The pressure difference can be generated using gravity, vacuum pressure, a mechanical pump, or any other method of generating a pressure difference known in the art. In addition, other methods to remove fluid from the reaction chamber may be used.

The fourth volume of fluid nominally has a cell concentration of zero. This can be accomplished using a filter that prevents removal of the cells from the reaction chamber, gravity or centrifugation to inertially to separate the cells from the fluid, or other methods known in the art to separate cells from a fluid.

If the first fluid comprises multiple source fluids, the multiple source fluids can be introduced to the reaction chamber individually and the sum of the total volume of the multiple source fluids is considered the first volume. Determination of the reaction chamber fluid product concentration can be performed through optical measurements such as optical absorption or scattering measurements, electrical measurements such as conductivity or impedance measurements, liquid chromatography, gas chromatography, weight, density, imaging, or any other method known to one skilled in the art.

In another aspect, the volume of sub-chamber A and sub-chamber B have a volume difference of delta-V. Starting from a condition where the volume in the reaction chamber is equal to the maximum volume of sub-chamber B, configuring sub-chamber B to its minimum volume forces the fluid to be in sub-chamber A, which can accept delta-V volume before becoming full. By configuring the sub-chamber A towards its maximum volume by applying vacuum to the upper-chamber A and opening the input valve, delta-V volume is drawn into the reaction chamber. The introduced fluid was then mixed by alternating pressurization of upper-chamber A and B and moving the fluid to be predominantly in the sub-chamber A and then in sub-chamber B. To remove delta-V through an output port, sub-chamber B is configured to its maximum volume by applying vacuum to upper-chamber B while sub-chamber A is configured towards its minimum volume by applying pressure to upper-chamber A. Because the maximum volume of sub-chamber B is delta-V less than the volume of fluid in the reaction chamber, delta-V volume remained in sub-chamber A. By opening an output valve, the excess delta-V volume of fluid was removed through an output conduit. By repeating this cycle every T seconds, an average volumetric flow rate delta-V/T can be achieved.

In a second aspect, the present invention relates to an apparatus where fluid flow control, fluid mixing, fluid filtering, and the reaction chamber are integrated into a microreactor device comprising a reaction chamber; an input conduit fluidically connecting an inlet to the microreactor device and a reaction chamber; a first output conduit fluidically connecting the reaction chamber and a first outlet of the microreactor device; a filter with a first side fluidically connected to the reaction chamber and a second side fluidically connected to a second outlet through a second output conduit; wherein the input conduit comprises an input valve to prevent fluid flow between the inlet and the reaction chamber; wherein the first output conduit comprises a first output valve to prevent fluid flow between the first outlet and the reaction chamber; wherein the second output conduit comprises a second output valve to prevent fluid flow between the second outlet and the second side of the filter; and an input pump to deliver a defined volume of fluid through the input conduit.

In a first preferred microreactor embodiment, the reaction chamber comprises: a first sub-chamber with a portion of a wall of the first sub-chamber defined by a first flexible member; a second sub-chamber with a portion of a wall of the second sub-chamber defined by a second flexible member; and a connection conduit fluidically connecting the first sub-chamber and second sub-chamber; a first position of the first flexible member that maximizes the volume of the first sub-chamber; a second position of the first flexible member that minimizes the volume of the first sub-chamber; an intermediate position of the first flexible member where the volume of the first sub-chamber is in between its minimum and maximum; a first position of the second flexible member that maximizes the volume of the second sub-chamber; and a second position of the second flexible member that minimizes the volume of the second sub-chamber; an intermediate position of the second flexible member where the volume of the second sub-chamber is in between its minimum and maximum; and a flexible member position generator to configure the positions of the flexible members.

A flexible member position generator is used to nominally configure the position of the flexible members. The position of the flexible members can also be constrained by the volume of fluid in the reaction chamber. In a first configuration of the flexible member position generator, the first flexible member would move to its first position and the second flexible member would move to its second position if the flexible members were not further constrained by the volume of fluid in the reaction chamber. For example, if the volume of fluid in the reaction chamber were greater than the maximum volume of the first sub-chamber, the second flexible member would not reach its second position because the excess volume would remain in the second sub-chamber. If the excess volume was to be removed, for example by opening a valve and allowing the excess volume to flow out of the second sub-chamber, the second flexible member would then move to its second position. In a second configuration of the flexible member position generator, the position of the first and second flexible members are not constrained by the flexible member position generator.

In a second preferred microreactor embodiment, comprising: the first preferred microreactor embodiment; a first upper chamber having a portion of a wall defined by the first flexible member and a portion of a wall defined by a first rigid retaining structure and adjacent to the first sub-chamber; and a second upper chamber having a portion of a wall defined by the second flexible member and a portion of a wall defined by a second rigid retaining structure and adjacent to the second sub-chamber; wherein: maximal deflection of the first position of the first flexible member is defined as the first flexible member substantially conforming to the first rigid retaining structure; wherein: maximal deflection of the first position of the second flexible member is defined as the second flexible member substantially conforming to the second rigid retaining structure; in the second position of the first flexible member, the first flexible member substantially conforms to a portion of the wall of the first sub-chamber such that the volume of the first sub-chamber is nominally zero; in the second position of the second flexible member, the second flexible member substantially conforms to a portion of the wall of the second sub-chamber such that the volume of the second sub-chamber is nominally zero;

The portions of the first flexible member and second flexible member that substantially conform to a wall of the first upper chamber and second upper-chamber respectively can be between 1% to 100% of the area of the flexible member, or between 1% and 100%, or between 50% and 100%, or between 80% and 100%.

In a third preferred microreactor embodiment comprising the second preferred embodiment, wherein the location of the filter and the location of the first end of the first output conduit are specified such that: the filter is located in the second sub-chamber; and the first end of the first output conduit is fluidically connected to the second sub-chamber such that fluid in the second sub-chamber can enter the first output conduit without passing through the filter.

In a fourth preferred microreactor embodiment comprising the second preferred embodiment, wherein the location of the filter and the location of the first end of the first output conduit are specified such that: the filter is located in the first sub-chamber; and the first end of the first output conduit is fluidically connected to the second sub-chamber such that fluid in the second sub-chamber can enter the first output conduit without passing through the filter.

In a fifth preferred microreactor embodiment comprising the third preferred embodiment wherein, the second flexible member in its second position prevents fluid flow between the filter and the first sub-chamber and prevents fluid flow between the first output conduit and the first sub-chamber.

In a sixth preferred microreactor embodiment comprising the fourth preferred embodiment wherein, the second flexible member in its second position prevents fluid flow between the first output conduit and the first sub-chamber.

In a bypass microreactor embodiment, comprising the first preferred microreactor embodiment, wherein the reaction chamber further comprises a bypass structure with a first portion fluidically connected to the first sub-chamber through a first bypass conduit comprising a first bypass isolation valve; and a second portion fluidically connected to the second sub-chamber through a second bypass conduit comprising a second bypass isolation valve; wherein, when the first and second bypass isolation valves are closed the bypass channel is fluidically isolated from the first and second sub-chambers. In this bypass microreactor embodiment, the second end of the input conduit is fluidically connected to the first portion of the bypass channel and the first end of the first output conduit is fluidically connected to the second portion of the bypass channel such that when the when the first and second bypass isolation valves are closed, the input conduit and first output conduit are fluidically isolated from the first and second sub-chambers and fluidically connected through the bypass structure. Preferably, the second end of the input conduit and the first end of the first output conduit are spatially separated by the length of the bypass structure.

Another aspect of the invention provides a method to operate the first through sixth microreactor embodiments to independently control the cell concentration and flow of fluid through the reaction chamber. The method comprises the steps of: A) closing the input, first output, and second output valve; B) configuring the flexible member position generator into a second configuration; C) opening the input valve; D) introducing a first volume of fluid into the reaction chamber with the input pump; E) closing the input valve; F) configuring the flexible member position generator into the first configuration; G) opening the first output valve; H) waiting for the positions of the flexible members to stop changing; I) closing the first output valve;

The method can further comprise the step: J) measuring the cell concentration in the reaction chamber.

The method can further comprise the steps: K) opening the second output valve; L) closing the second output valve; M) using the input pump to introduce a second volume of fluid into the reaction chamber Starting from an IDLE condition where the input valve, first output valve, and second output valve are closed and the flexible member position generator is not in its first configuration, the steps of the method can be executed in the following sequence to operate the microreactor embodiment in a turbidostat cycle: 1) step A; 2) step J; 3) if the measured cell concentration is less than a target cell concentration then stop and enter the IDLE condition, otherwise continue; 4) step B; 5) step C; 6) step D; 7) step E; 8) step F; 9) step G; 10) step H; 11) step I; 12) finished enter the IDLE condition.

Starting from the IDLE condition, the steps of the method can be executed in the following sequence to operate the microreactor embodiment in a chemostat cycle: 1) step A; 2) step B; 3) step C; 4) step D; 5) step E; 6) step F; 7) step G; 8) step H; 9) step I; 10) finished enter the IDLE condition.

Starting from the IDLE condition, the steps of the method can be executed in the following sequence to operate the microreactor embodiment in a perfusion cycle: 1) step A; 2) step B; 3) step C; 4) step M; 5) step E; 6) step F; 7) step K; 8) step H; 9) step L; 10) finished enter the IDLE condition.

The turbidostat cycle, chemostat cycle, and perfusion cycle can be operated repeatedly with a time interval between the execution of each cycle.

When operating a bypass microreactor embodiment, the method can further comprise the steps: N) closing the first and second bypass isolation valves; M) opening the first and second bypass isolation valves.

Starting from a bypass IDLE condition where the input valve, first output valve, and second output valves are closed, and the first and second bypass isolation valves are open, and the flexible member position generator is not in its first configuration, the steps of the method can be executed in the following sequence to operate the bypass microreactor embodiment in a bypass turbidostat cycle: 1) step A; 2) step J; 3) if the measured cell concentration is less than a target cell concentration then stop and enter the bypass IDLE condition, otherwise continue; 4) step N; 5) step C; 6) step G; 7) step D; 8) step E; 9) step I; 10) step M; 11) finished enter the bypass IDLE condition.

Starting from the bypass IDLE, the steps of the method can be executed in the following sequence to operate the bypass microreactor embodiment in a bypass chemostat cycle: 1) step N; 2) step C; 3) step G; 4) step D; 5) step E; 6) step I; 7) step M; 9) finished enter the bypass IDLE condition.

Starting from the bypass IDLE condition, the steps of the method can be executed in the following sequence to operate the bypass microreactor embodiment in a bypass perfusion cycle: 1) step A; 2) step B; 3) step C; 4) step M; 5) step E; 6) step F; 7) step K; 8) step H; 9) step L; 10) finished enter IDLE condition.

The bypass turbidostat cycle, bypass chemostat cycle, and bypass perfusion cycle can be operated repeatedly with a time interval between the execution of each cycle.

In a third aspect, the present invention relates to a microreactor embodiment integrating additional components comprising an input pump located between an inlet to the microreactor and the reaction chamber and fluidically connected to the input and the reaction chamber, a first output valve located between the reaction chamber and the first output and fluidically connected to the reaction chamber and the first output, and a second output valve located between the filter and the second output and fluidically connected between the filter and the second output.

The reaction chamber of the microreactor comprises a first chamber with at least a portion of a wall of the first chamber defined by a first flexible member, a second chamber adjacent to the first chamber with at least a portion of a wall defined by the first flexible member a third chamber with at least a portion of a wall of the third chamber defined by a second flexible member, and a fourth chamber adjacent to the third chamber with at least a portion of a wall defined by the second flexible member.

The first chamber is fluidically connected to the input pump and the third chamber is fluidically connected to the first chamber, the filter, and first output. The third chamber can also be fluidically connected to the input pump.

The input pump can be a peristaltic pump, a gravity or pressure pump, an osmotic pressure pump, or any other type known to one skilled in the art. The valves can be mechanical valves, peristaltic valves, electrical valves, magnetic valves, osmotic valves, or any other type known to one skilled in the art. Flexible member can also be formed of a variety of materials. In some embodiments, all or part of the flexible member can be formed of a polymeric material. In some embodiments, the flexible member can comprise an elastomeric material, for example, having a Young's modulus of less than about 1 GPa. A variety of elastomeric polymeric materials are suitable for making the flexible member including, for example, polymers of the general classes of silicone polymers, epoxy polymers, and acrylate polymers.

In another aspect, a method is provided to operate the microbioreactor to control cell concentration. The first and second output valves are closed. Fluid is added via the input by the pump. The second flexible member is strained by a pressure differential between the fourth chamber and the third chamber such that the pressure in the fourth chamber is greater than the pressure in the third chamber. The first flexible member is strained by fluid addition into the first chamber via the fluid communication with the third chamber. This strain can cause a portion the first flexible member to substantially conform to a wall of the second chamber. The first output valve is opened causing a portion of the second flexible member to substantially conform to a wall of the third chamber. Fluid remaining in the third chamber is removed via the first output. The first output valve is closed and the pressure differential between the third chamber and fourth chamber is reduced. Fluid is added via the input by the pump. The second flexible member is strained by a pressure differential between the fourth chamber and the third chamber such that the pressure in the fourth chamber is greater than the pressure in the third chamber. The first flexible member is strained by fluid addition into the first chamber via fluid communication with the third chamber. The first flexible member substantially conforms to a wall of the second chamber. The second output valve is opened and the second flexible member substantially conforms to a wall of the third chamber. Remaining fluid in the third chamber is removed via the filter and through the second output. The second output valve is closed and the pressure differential between the third chamber and fourth chamber is reduced.

When the second flexible member is strained, the pressure differential between the fourth chamber and third chamber can be between 0.1 psi and 30 psi, or between 0.5 psi and 15 psi, or between 1 psi and 10 psi. The portions of the first flexible member and second flexible member that substantially conform to a wall of the second chamber and third chamber respectively can be between 1% to 100% of the area of the flexible member, or between 10% and 100%, or between 50% and 100%, or between 80% and 100%. When the pressure differential between the third chamber and fourth chamber is reduced, it can be reduced by between 10% and 100%, or between 50% and 100%, or between 90% and 100% of the pressure differential before reduction.

To measure optical density in the reaction chamber for turbidostat control, the apparatus and methods described in US20130194575 A1 are used where the deformation of the flexible member of a sub-chamber provides a reconfigurable optical path.

DEFINITIONS

The following definitions and examples for terms in the description are provided for additional clarity:

reaction chamber: this term refers to a volume in which a chemical, biochemical, or cell culture or fermentation reaction takes place. A reaction chamber comprises one or more sub-chambers or structures that are fluidically coupled, or intermittently fluidically coupled.

Sub-chamber: this term refers to a chamber that is a portion of a reaction chamber.

Fluid path: this term refers to a path from a start point to an end point that is entirely within a fluid.

Fluidic connection: this term refers to a fluid path where the start point of the fluid path is one item being connected and the end point of the fluid path is another item being connected.

Filter: this term refers to a structure with a first side and a second side where the passage of a substance through the filter is restricted. An example is a material with a plurality of pores with a maximum pore size of 1 um that restricts the passage of particles larger than 1 um from passing through the material, while particles smaller than 1 um may pass through.

conduit: this term refers to a mechanical structure that encloses a fluid path. Examples are a pipe, or a tube, or an enclosed channel. The mechanical structure need not be a single structure and can be different mechanical structures joined together so long as a fluid path is enclosed by the structure. For example, a first pipe connected to a valve connected to a tube, connected to a second pipe would represent a conduit connecting an open end of the first pipe to an open end of the second pipe. Furthermore, a conduit may enclose more than one fluid path. For example, when a valve that is part of a conduit is closed, two fluid paths are formed. One from a first end of the conduit to the first side of the valve and another from a second side of the valve to a second end of the conduit.

valve: a valve is a device that in a closed state can prevent fluid flow from a first portion of a conduit to a second portion of a conduit, while in an open state fluid may flow from a first portion of a conduit to a second portion of a conduit. For example a ball valve, a pinch valve, or a membrane pinch valve comprising a flexible portion of a conduit that can be deformed to close the conduit. Deformation of the flexible portion of the conduit may be achieved by pressurizing a valve chamber adjacent to the flexible portion of the conduit. It should be understood that in the description of microreactor embodiments using membrane pinch valves, reference to a valve should be considered equivalent to the more precise statement: valve defined by a conduit and a flexible member adjacent to the valve chamber.

input pump: This term refers to a device with an input and an output that can move a determined volume of fluid from the input to the output. For example, a standard laboratory peristaltic pump similar to U.S. Pat. No. 4,278,085 comprises a flexible tube and a movable roller. The roller compresses the flexible tube such that the flexible tube is closed where the roller compressing the flexible tube. As the roller moves forward, translating the compressed point along the tube, the fluid in front of the compressed point is moved forward. In a preferred embodiment, input pump comprises a conduit further comprising a first membrane pinch valve, a second membrane pinch valve, and a third membrane pinch valve. The input pump may be integral to the first conduit of a microreactor embodiment and the input pump may comprise the input valve of a microreactor embodiment.

flexible member: this term refers to a portion of a chamber that can move, whereby the movement of the portion of the chamber changes the internal volume of the chamber. The possible positions of the flexible member can be constrained by the mechanical properties of the flexible member, external structures that would prevent the motion of the flexible member, characteristics of the means used to change the position of the flexible member, a constraint on the internal volume of the chamber, or a combination of these constraints. Excluding constraints on the position of the flexible member due to a constraint on the internal volume of the chamber, the constraints on the position of the flexible member determine a maximum volume position of the flexible member where the internal volume of the chamber is maximized and a minimum volume position of the flexible member where the internal volume of the chamber is minimized. Flexible member can also be formed of a variety of materials. In some embodiments, all or part of the flexible member can be formed of a polymeric material. In some embodiments, the flexible member can comprise an elastomeric material, for example, having a Young's modulus of less than about 1 GPa. A variety of elastomeric polymeric materials are suitable for making the flexible member including, for example, polymers of the general classes of silicone polymers, epoxy polymers, and acrylate polymers.

3-way solenoid switch: a mechanical device comprising a common port, a normally open port, and a normally closed port. when the switch is not energized, the common port and normally open port are fluidically connected, referred to as an open state. when the switch is energized, the common port and normally closed port are fluidically connected, referred to as a closed state.

flexible member position generator: This term refers to an apparatus configured to change the position of a flexible member. In a preferred embodiment, a position generator for a flexible member comprises: a first 3-way solenoid switch comprising a first common port, a first normally open port, and a first normally closed port; a first pressure source fluidically connected to the first normally closed port; an upper chamber adjacent to the flexible member that is fluidically connected to the first common port. In a preferred embodiment, the position generator for a flexible member can further comprise a second 3-way solenoid valve with a second normally closed port fluidically connected to a second pressure source, a second common port fluidically connected to the first normally open port, and a second normally open port vented to atmosphere. A configuration of the position generator is then determined by the state of the solenoid switches. In a preferred embodiment. The pressure of the first pressure source is selected to reduce the volume of the chamber and the pressure of the second pressure source is selected to increase the volume of the chamber. In a first configuration, the first 3-way solenoid switch is set to an open state and the second 3-way solenoid switch is set to a closed state. In this first configuration the volume of the chamber increases. In a second configuration the first 3-way solenoid switch is set to a closed state and the second 3-way solenoid switch is set to an open state. In this second configuration, the volume of the chamber decreases. In a third configuration both 3-way solenoid switches are set to an open state. In this third configuration the volume of the chamber is not constrained by the position generator. It should be clear to one of ordinary skill in the art that multiple position generators for multiple flexible members may be combined into a compound position generator, where the overall state of the position generator is composed of the states of the position generators for each flexible member. It should also be clear to one of ordinary skill in the art that alternative connections of 3-way solenoid switches or other switches may be used to change the position of a flexible member.

valve state: This term refers to the open/closed state of each of the valves of the microbioreactor embodiment or bypass microbioreactor embodiment.

maximum volume of a sub-chamber: This term refers to the volume of a sub-chamber of the reaction chamber with a portion of a wall comprising a flexible member, wherein the flexible member is in a position such that no increase in volume may be achieved by changing the state of the position generator or the valve state of the microbioreactor embodiment.

minimum volume of a sub-chamber: This term refers to the volume of a sub-chamber of the reaction chamber with a portion of a wall comprising a flexible member, wherein the flexible member is in a position such that no decrease in volume may be achieved by changing the state of the position generator or the valve state of the microbioreactor embodiment.

nominally zero volume: This term refers to a condition where the volume of a chamber is less than 10% of the maximum volume of the chamber, or less than 1% of the maximum volume of the chamber, or less than 0.1% of the maximum volume of the chamber, or less than 0.01% of the maximum volume of the chamber, or less than 0.001% of the maximum volume of the chamber. In this condition, the remaining volume in the chamber could be from a thin film of fluid remaining in the chamber, or fluid trapped in small imperfections or small structures inside the chamber.

bypass structure: this term refers to a structure comprising a bypass chamber with a fixed volume that encloses a fluid path between the input conduit and the first output conduit, wherein the fluid path does not pass through the first sub-chamber or second sub-chamber. The bypass structure further comprises a first bypass conduit fluidically connecting a first portion of the bypass chamber to a first sub-chamber and a second bypass conduit fluidically connecting a second portion of the bypass chamber to a second sub-chamber. The first bypass conduit further comprises a first bypass isolation valve and the second bypass conduit further comprises a second bypass isolation valve. In a first configuration of the bypass structure, the first and second bypass isolation valves are closed which fluidically isolates the bypass chamber from the reaction chamber. In this configuration, there is a fluid path from the inlet to an outlet when the input valves and output valve are open. In a second configuration of the bypass structure, the bypass isolation valves are open and the input valves and output valve are closed. In this second configuration there is a fluid path between the first and second sub-chamber that is enclosed by the bypass chamber. When the reaction chamber is mixed by alternately pressurizing the first and second upper chamber, fluid flows in the connecting conduit and the bypass chamber. In a preferred embodiment, the fluid resistance along the fluid path enclosed by the bypass chamber and the fluid resistance along the connecting conduit are comparable. In a preferred embodiment, the bypass structure is an elongated chamber with one spatial dimension at least ten times larger than either of the other two spatial dimensions of the chamber.

Dilution rate: this term refers to the flow rate through a reaction chamber divided by the volume of the reaction chamber.

Preventing fluid flow in a conduit: this phrase describes a condition where fluid is not able to flow in the conduit and can arise under a variety of conditions. One condition is when a valve along the conduit is closed. Another condition is when an external pump stops pumping fluid.

Configuring valve states: This phrase refers a point in time when referenced valves are in specified states. Unreferenced valves may be open or closed. The order of setting individual valves to reach a given configuration and the timing of setting individual valves to reach a given configuration are not specified.

What is claimed is:

1. A microreactor apparatus to perform a continuous bioreaction process in a fluid wherein the dilution rate of cells and the dilution rate of a product can be different, comprising:
a reaction chamber comprising a first sub-chamber having a reconfigurable first volume fluidically coupled through a connecting conduit to a second sub-chamber having a reconfigurable second volume;
an input conduit fluidically connecting an inlet to the microreactor apparatus to the reaction chamber;
a first output conduit fluidically connecting the reaction chamber to a first outlet of the microreactor apparatus;
a filter that restricts the passage of cells from a first side of the filter to a second side of the filter, wherein the first side is fluidically connected to the reaction chamber and the filter is mounted such that all fluid paths from the reaction chamber to the second side of the filter pass through the filter; and a second output conduit fluidically connecting the second side of the filter to a second outlet of the microreactor.

2. The apparatus of claim 1 wherein the maximum volume of the sub-chambers is between approximately 100 microliters and 10 mililiters.

3. The apparatus of claim 1 where the maximum volume of the first sub-chamber is different than the maximum volume of the second sub-chamber.

4. The apparatus of claim 3 where the volume difference between the first and second sub-chamber is between 0 microliters and 1 milliliter.

5. The apparatus of claim 1 wherein a portion of the interior boundary of a sub-chamber comprises a flexible member;
whereby the deformation of the flexible member changes the internal volume of the sub-chamber.

6. The apparatus of claim 5 further comprising a retaining structure to constrain the position of the flexible member;
whereby deformation of the flexible member such that it substantially conforms to the inner boundary of the retaining structure results in a maximal volume of the sub-chamber.

7. The apparatus of claim 1 where the input conduit further comprises an input valve, wherein closing the input valve prevents fluid flow between portions of the input conduit on opposite sides of the input valve.

8. The apparatus of claim 7 wherein the input conduit further comprises a first pump valve and a second pump valve, wherein closing the first pump valve reduces the volume of the input conduit by a first pump volume.

9. The apparatus of claim 1 where the first output conduit further comprises a first output valve, wherein closing the first output valve prevents fluid flow between portions of the first output conduit on opposite sides of the first output valve.

10. The apparatus of claim 1 where the second output conduit further comprises a second output valve, wherein closing the second output valve prevents fluid flow between portions of the second output conduit on opposite sides of the second output valve.

11. The apparatus of claim 1 wherein a portion of the interior boundary of a sub-chamber comprises the first side of the filter.

12. The apparatus of claim 1 wherein particles smaller than 0.2 microns may pass through the filter.

13. The apparatus of claim 1 wherein particles smaller than one micron may pass through the filter.

14. The apparatus of claim 1 wherein particles smaller than ten microns may pass through the filter.

15. The apparatus of claim 1, wherein the input conduit is physically connected to the first sub-chamber and the first output conduit is physically connected to the second sub-chamber, further comprising:
an input valve in the input conduit;
a first bypass isolation valve in the input conduit between the input valve and the first sub-chamber;
an output valve in the first output conduit;
a second bypass isolation valve in the first output conduit between the output valve and the second sub-chamber; and
a bypass structure fluidically connected to the input conduit with a physical connection to the input conduit between the first bypass isolation valve and the input valve, and fluidically connected to the first output conduit with a physical connection to the first output conduit between the second bypass isolation valve and the output valve, wherein the volume of the bypass structure is fixed;
wherein closing the first and second bypass isolation valves fluidically isolates the bypass structure from the reaction chamber; and
wherein opening the first and second bypass isolation valves and closing the input valve and the first output valve fluidically connects the first sub-chamber, the second sub-chamber and the bypass structure.

16. A method for using the apparatus of claim 15 to perform a continuous reaction process comprising the steps:
(xii) configuring the first and second bypass isolation valves to be in a closed state and the input valve and first output valve to be in an open state;
(xiii) introducing a volume of fluid less than the volume of the bypass chamber into the bypass chamber; and
(xiv) configuring the first and second bypass isolation valves to be in an open state and the input valve and first output valve to be in a closed state.

17. The method of claim 16 further comprising the steps:
(xv) configuring a bypass isolation valve and the input valve to be in an open state and the first output valve to be in a closed state;
(xvi) configuring a sub-chamber in a first configuration whereby the volume of the sub-chamber is driven to be minimal; and
(xvii) configuring the input valve and first output valve to be in a closed state and configuring the second output valve in an open state.

18. A method for using the apparatus of claim 1 to perform a continuous reaction process comprising the steps:
(i) Configuring the first sub-chamber in a first configuration whereby the volume of the first sub-chamber is driven to be minimal;
(ii) Introducing a fluid into the reaction chamber;
(iii) Preventing fluid flow in any output conduit;
(iv) Preventing fluid flow in the input conduit and any output conduit;
(v) Preventing fluid flow in the input conduit and preventing fluid flow in the first output conduit; and
(vi) Preventing fluid flow in the input conduit and preventing fluid flow in the second output conduit.

19. The method of claim 18 further comprising the step:
(vii) Configuring the second sub-chamber in a second configuration where the volume of the second sub-chamber is driven to be maximal.

20. The method of claim 18 further comprising the steps
(viii) Configuring the second sub-chamber in a first configuration where the volume of the second sub-chamber is driven to be minimal;
(ix) Configuring the first sub-chamber in a second configuration where the volume of the first sub-chamber is driven to be maximal;
(x) Configuring the first sub-chamber in a third configuration where the volume of the first sub-chamber is free to change between a minimum and maximum volume; and
(xi) Configuring the second sub-chamber in a third configuration where the volume of the second sub-chamber is free to change between a minimum and maximum volume.

* * * * *